United States Patent
Suh et al.

(10) Patent No.: US 9,482,618 B2
(45) Date of Patent: Nov. 1, 2016

(54) SINGLE NANOPARTICLE HAVING A NANOGAP BETWEEN A CORE MATERIAL AND A SHELL MATERIAL, AND PREPARATION METHOD THEREOF

(75) Inventors: Yung Doug Suh, Daejeon (KR); Jwa Min Nam, Seoul (KR); Dong Kwon Lim, Gyeonggi-do (KR); Ki Seok Jeon, Daejeon (KR)

(73) Assignees: KOREA RESEARCH INSTITUTE OF CHEMICAL TECHNOLOGY, Daejeon (KR); SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 13/989,709

(22) PCT Filed: Nov. 24, 2011

(86) PCT No.: PCT/KR2011/009031
§ 371 (c)(1),
(2), (4) Date: Aug. 19, 2013

(87) PCT Pub. No.: WO2012/070893
PCT Pub. Date: May 31, 2012

(65) Prior Publication Data
US 2013/0330839 A1    Dec. 12, 2013

(30) Foreign Application Priority Data
Nov. 24, 2010 (KR) ................ 10-2010-0117527

(51) Int. Cl.
C12M 1/36    (2006.01)
G01N 21/65   (2006.01)
(Continued)

(52) U.S. Cl.
CPC ......... *G01N 21/658* (2013.01); *A61K 49/0002* (2013.01); *G01N 33/54346* (2013.01); *G01N 2021/653* (2013.01)

(58) Field of Classification Search
CPC ................ G01N 21/658; G01N 33/54346
USPC ....................... 435/287.2; 422/82.05
See application file for complete search history.

(56) References Cited

U.S. PATENT DOCUMENTS

| 5,306,403 A | 4/1994 | Vo-Dinh |
| 6,002,471 A | 12/1999 | Quake |

(Continued)

FOREIGN PATENT DOCUMENTS

| JP | 2008-284411 | * 11/2008 |
| JP | 2009537135 A | 10/2009 |

(Continued)

OTHER PUBLICATIONS

Lim et al "DNA-embedded Au/Ag core-shell nanoparticles" ChemComm, 2008, 5312-5314.*

(Continued)

*Primary Examiner* — Betty Forman
(74) *Attorney, Agent, or Firm* — Ladas & Parry LLP

(57) ABSTRACT

The present invention is to provide a nanoparticle, which can be used effectively for Raman analysis based on very high amplification effect of electromagnetic signal by plasomonic coupling of nanogap formation inside thereof and high reproducibility, and which includes core and surrounding shell with nanogap formation between the same and the method of synthesis thereof. The present invention is also to provide the method for detecting the analyte using the above nanoparticle and the analyte detection kit including the above nanoparticle.

20 Claims, 25 Drawing Sheets

(51) Int. Cl.
G01N 33/543 (2006.01)
A61K 49/00 (2006.01)

(56) References Cited

U.S. PATENT DOCUMENTS

| | | | |
|---|---|---|---|
| 6,040,191 A | 3/2000 | Grow | |
| 6,149,868 A | 11/2000 | Natan et al. | |
| 6,174,677 B1 | 1/2001 | Vo-Dinh | |
| 6,313,914 B1 | 11/2001 | Roe | |
| 2004/0057903 A1* | 3/2004 | Hancu et al. | 424/9.3 |
| 2006/0105170 A1* | 5/2006 | Dobson et al. | 428/403 |
| 2006/0148104 A1* | 7/2006 | Marini et al. | 436/524 |
| 2010/0227416 A1 | 9/2010 | Koh et al. | |
| 2011/0124008 A1* | 5/2011 | Nam et al. | 435/7.1 |
| 2011/0200534 A1* | 8/2011 | Cheon et al. | 424/9.32 |
| 2012/0014878 A1* | 1/2012 | Culha | 424/9.1 |

FOREIGN PATENT DOCUMENTS

| | | | |
|---|---|---|---|
| KR | 10090116653 A | | 11/2009 |
| WO | 2007135593 A1 | | 11/2007 |
| WO | 2008116093 A2 | | 9/2008 |
| WO | WO2009/136741 | * | 11/2009 |
| WO | WO2010/109268 | * | 9/2010 |

OTHER PUBLICATIONS

Kahraman et al "Oligonucleotide-Mediated Au—Ag Core-Shell Nanoparticles" Plasmonics, Oct. 6, 2009, 4: 293-301.*
Shuming Nie, et al; "Probing Single Molecules and Single Nanoparticles by Surface-Enhanced Raman Scattering", Science, vol. 275; Feb. 21, 1997, pp. 1102-1106.
Katrin Kneipp, et al; "Single Molecule Detection Using Surface-Enhanced Raman Scattering (SERS)", Physical Review Letters, vol. 78, No. 9, Mar. 3, 1997, pp. 1667-1670.
Yunwei Charles Cao, et al; "Nanoparticles with Raman Spectroscopic Fingerprints for DNA and RNA Detection", Science, vol. 297, Aug. 30, 2002, pp. 1536-1540.
William E. Doering, et al; "Single-Molecule and Single-Nanoparticle SERS: Examining the Roles of Surface Active Sites and Chemical Enhancement", J. Phy. Chem. B., vol. 106, pp. 311-317, Published on Web Dec. 14, 2001.
Ying Fang et al; "Measurement of the Distribution of Site Enhancements in Surface-Enhanced Raman Scattering", Science, vol. 321, Jul. 18, 2008, pp. 388-392.
Ken A. Bosnick, et al; "Fluctuations and Local Symmetry in Single-Molecule Rhodamine 6G Raman Scattering on Silver Nanocrystal Aggregates", J. Phys. Chem. B., vol. 106, pp. 8096-8099, Published on Web Jun. 27, 2002.
Sarah J. Hurst, et al; "Maximizing DNA Loading on a Range of Gold Nanoparticle Sizes", Analytical Chemistry, vol. 78, No. 24, pp. 8313-8318, Published on Web: Nov. 10, 2006.
Guoguang Rong, et al; "Nanoscale porous silicon waveguide for label-free DNA sensing", Biosensors and Bioelectronics, vol. 23, pp. 1572-1576, Available online Jan. 24, 2008.
Zidong Wang, et al; "DNA-Mediated Control of Metal Nanoparticle Shape: One-Pot Synthesis and Cellular Uptake of Highly Stable and Functional Gold Nanoflowers", NanoLetters, vol. 10, pp. 1886-1891, Published on Web: Apr. 20, 2010.
Arnd Schimanski, et al; "Interactions between $[AuX_4]^-$ (X=Cl, Cn) and cytosine and guanine model necleobases: salt formation with (hemi-) protonated bases, coordination, and oxidative degradation of quinine", Inorganica Chimica Acta, vol. 283, pp. 223-232, Dec. 1, 1998.
Kenneth R. Brown, et al; "Hydroxylamine Seeding of Colloidal Au Nanoparticles in Solution and on Surfaces", Langmuir, vol. 14, pp. 726-728, Published on Web: Jan. 22, 1998.
Zhanfang MA, et al; "Naked-Eye Sensitive Detection of Immunoglubulin G by Enlargement of Au Nanoparticles In Vitro", Agnew. Chem. Int. Ed., vol. 41, No. 12, pp. 2176-2179; Article first online: Jun. 12, 2002.
Kristin L. Wustholz, et al; "Structure-Activity Relationships in Gold Nanoparticle Dimers and Trimers for Surface-Enhanced Raman Spectroscopy", Journal American Chemical Society, vol. 132, pp. 10903-10910; Published on Web: Jul. 21, 2010.
Yannick Sonnefraud, et al; "Experimental Realization of Subradiant, Superradiant, and Fano Resonances in Ring/Disk Plasmonic Nanocavities", ACS Nano, vol. 4, No. 3, pp. 1664-1670; Published online: Feb. 15, 2010.
Dong-Kwon Lim, et al; "Nanogap-engineerable Raman-active nanodumbbells for single-molecule detection", Nature Materials, vol. 9, pp. 60-67; Published online: Dec. 13, 2009.
Peng Zhang, et al; "Surface-Enhanced Raman Scattering inside Metal Nanoshells", J. Am. Chem. Soc., vol. 131, pp. 3808-3809; Published on Web; Feb. 25, 2009.
Cristina L. Zavaleta, et al; "Multiplexed imaging of surface enhanced Raman scattering nanotags in living mice using noninvasive Raman spectroscopy", PNAS, vol. 106, No. 32, pp. 13511-13516, Aug. 11, 2009.
Karen Faulds, et al; "Evaluation of Surface-Enhanced Resonance Raman Scattering for Quantitative DNA Analysis", Analytical Chemistry, vol. 76, No. 2, pp. 412-417, Published on Web: Dec. 6, 2003.
T. Dadosh, et al; "Plasmonic Control of the Shape of the Raman Spectrum of a Single Molecule in a Silver Nanoparticle Dimer", ACS Nano, vol. 3, No. 7, pp. 1988-1994; Published online Jun. 17, 2009.
Dong-Kwon Lim, et al; "Highly uniform and reproducible surface-enhanced Raman scattering from DNA-tailorable nanoparticles with 1-nm interior gap", Nature Nanotechnology, vol. 6, pp. 452-460, Published online May 29, 2011.
Dan Feldheim; "Assembly of Metal Nanoparticle Arrays Using Molecular Bridges", The Electrochemical Society Interface, Fall 2001, pp. 22-25.
P.B. Johnson, et al "Optical Constants of the Noble Metals,", Physical Review B, vol. 6, No. 12, Dec. 15, 1972, pp. 4370-4379.
P.G. Etchegoin, et al; "An analytic model for the optical properties of gold", The Journal of Chemical Physics, vol. 125, pp. 164705-1 to 164705-3; Published online: Oct. 24, 2006.
International Search Report mailed Jul. 9, 2012; PCT/KR2011/009031.
Weili Shi et al., "Gold Nanoshells on Polystyrene Cores for Control of Surface Plasmon Resonance", Langmuir vol. 21, Published on Web Jan. 15, 2005, pp. 1610-1617.
Japanese Office Action Issued Aug. 5, 2014; Appln. No. 2013540896.

* cited by examiner

Two different nanogap structures in solution

Multiple, fluctuating *point* gap junctions with different, non-uniform SERS

Conventional Multi-meric Nanostructure with Inter-Nanogaps

Vs.

Uniform, large *surface* gap junction for highly robust and quantitative SERS

Intra-Nanobridged Nanogap Core-Shell Nanostructure

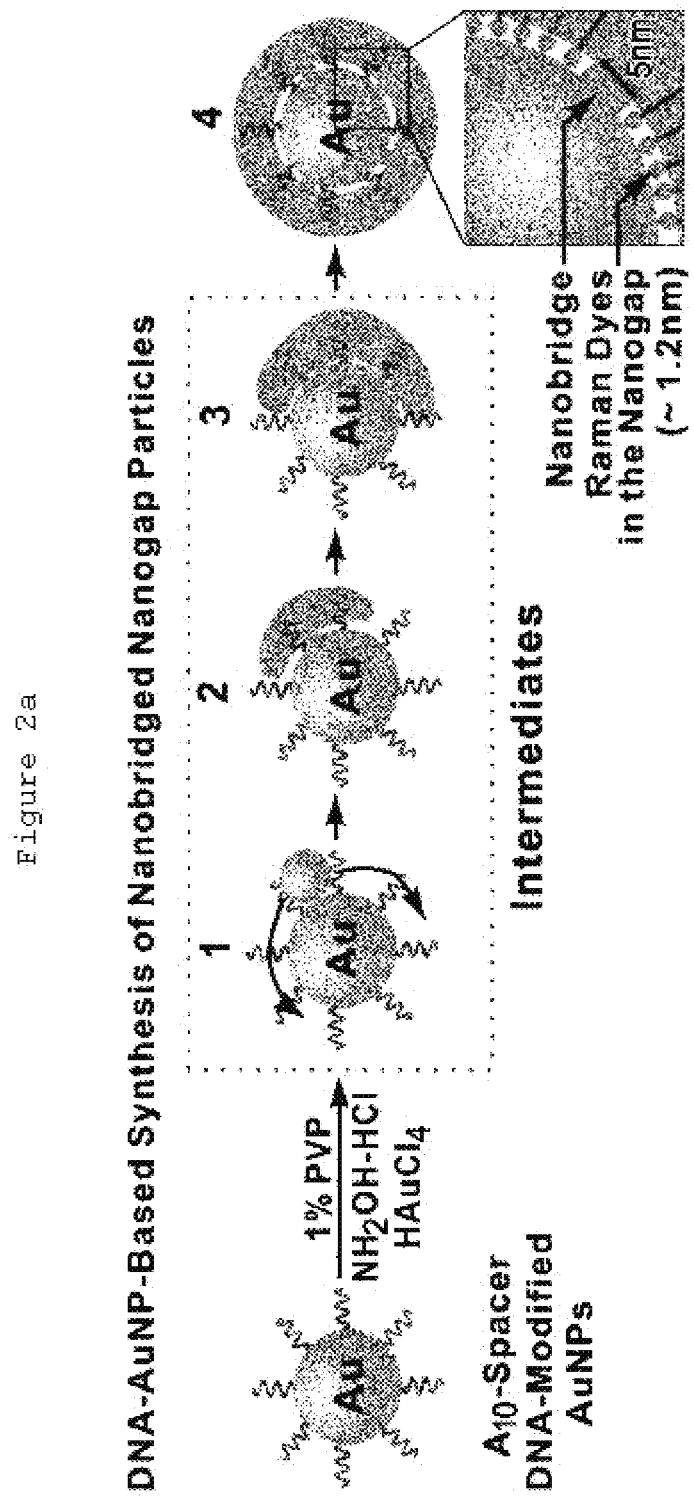

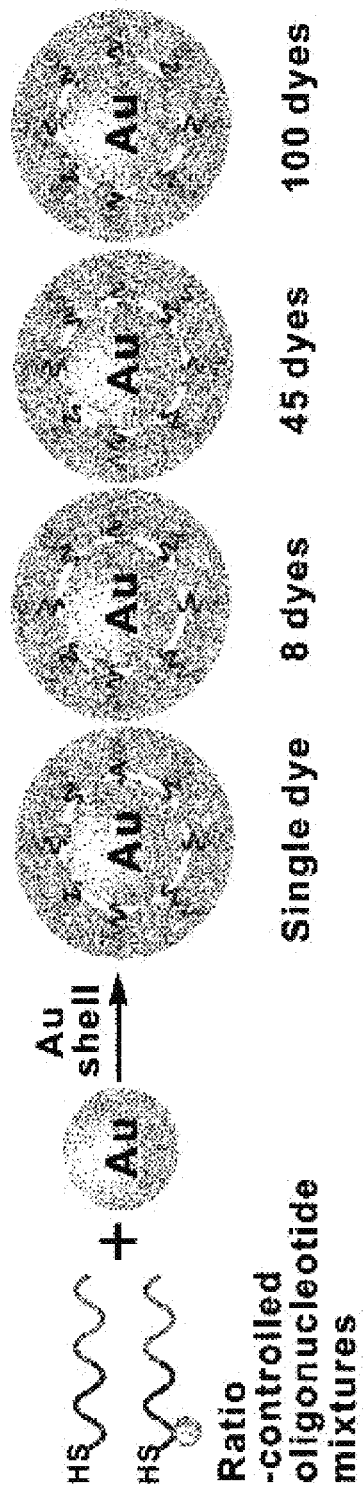

SINGLE NANOPARTICLE HAVING A NANOGAP BETWEEN A CORE MATERIAL AND A SHELL MATERIAL, AND PREPARATION METHOD THEREOF

TECHNICAL FIELD

The present invention relates to a single nanoparticle, which has extremely high amplifying capability of electromagnetic signal by plasomonic coupling of the nanogap formed between core material and shell material and which shows the homogeneous signal intensity and quantitative signal contrasted with concentration of particle caused by homogeneous distribution and quantitative control of signal substance on the surface of core material, and preparation method thereof.

BACKGROUND ART

Highly accurate detection of single molecules from biological sample and other samples can be widely used in medical diagnostics, pathology, toxicology, environmental sampling, chemical analysis, and many other areas, and nanoparticles and chemicals labeled with specific substances have been used in researches for metabolism, distribution and coupling of small amounts of synthetic substances and bio-molecules in biochemistry for last a few years. Typically, there are methods using radioactive isotopes, organic fluorescent materials and quantum dots which are inorganic materials.

$^3H$, $^{14}C$, $^{32}P$, $^{35}S$ and $^{125}I$, which are radioactive isotopes of $^1H$, $^{12}C$, $^{31}P$ and $^{127}I$ extensively found in the living body, are widely used as radioactive indicators in the method using radioactive isotopes. Radioactive isotopes have been used for a long time because of the similar chemical properties with non-radioactive isotope, which enables a random replacement, and relatively large emission energy, which enables the detection of small amounts. However, it is not easy to handle because of the harmful radiation and the radiation of some isotopes has short half-life instead of large emission energy, causing inconvenience in long-term storage or experiment.

Organic fluorescent dyes are widely used as alternatives to radioactive isotopes. Fluorescent dyes emit light with unique wavelength when activated by light with specific wavelength. Particularly, while radioactive material expresses the limitation in the detection, requiring long detection time with miniaturization of detection device, fluorescent dyes emit thousands of photons per molecules under appropriate conditions and theoretically enable the detection even at the level of a single-molecule. However, the fluorescent dyes have limitations in that the fluorescent dyes are connected by deformation of the part which relatively little affects the activity through structure activity relationship, incapable of direct substitution of the elements of the active ligand as radioactive isotopes. In addition, these fluorescent markers emit weaker intensity of fluorescence over time (photobleaching) and have a very narrow wavelength range of activation light and a wide wavelength range of emission light leading to the disadvantage of interference between different fluorophores. Also, the number of available fluorophores is extremely limited.

Also, semiconductor nano materials, quantum dots, is composed of CdSe, CdS, ZnS, ZnSe, etc. and emit lights of different colors depending on the size and type. Quantum dots, with wide active wavelengths and narrow emission wavelength compared to organic fluorescent dyes, have larger number of cases in which light of different colors are emitted than organic fluorescent dyes. In recent years, therefore, quantum dots have been used as a way to overcome the shortcoming of organic fluorescent dyes. However, they have disadvantages of high toxicity and difficulty of mass production. In addition, the number of available quantum dots, although theoretically variable, is highly restricted in practice.

To overcome such problems, Raman Spectrometry and/or Surface Plasmon Resonance have been recently used for labeling.

Among them, Surface Enhanced Raman Scattering (SERS) is the spectroscopy using the phenomenon that the intensity of Raman scattering increases rapidly by more than $10^6$ to $10^8$ times when the molecule is adsorbed on the roughened surface of metallic nanostructure of gold, silver, etc. When the light passes through a concrete medium, a certain amount of light deviates from an unique direction, which is known as Raman scattering. Since some of the scattered light is absorbed and excites an electron to the higher level of energy, the wavelength of Raman emission spectrum is different from that of stimulated light and represents the chemical composition and structural properties of light absorbing molecule in the sample. Therefore, Raman spectroscopy, combined with rapidly advancing current nanotechnology, can be developed into the highly sensitive technology to detect directly a single molecule and is largely expected to be used especially as crucial medical sensor. The Surface Enhanced Raman Scattering (SERS) is related to plasmon resonance phenomenon, and since wherein metal nanoparticles shows the pronounced optical resonance in response to the incident electromagnetic radiation by group coupling of metal conduction electrons in the metal, the nanoparticles of gold, silver, copper and certain other metals can be used essentially as a small antenna to improve focusing effects of electromagnetic radiation. Molecules located in the vicinity of these particles represent a much greater sensitivity for Raman spectroscopy analysis.

Therefore, the researches for early diagnosis of various disease-associated genes and proteins (biomarkers) using SERS sensors are actively carried out. Unlike the other analysis methods (infrared spectroscopy), Raman spectroscopy has several advantages. While infrared spectroscopy obtains a strong signal in the case of molecules with change in the molecular dipole moment, Raman spectroscopy can obtain a strong signal even in the case of non-polar molecule, resulting that almost all organic molecules have a unique Raman shift ($cm^{-1}$). In addition, because it is not affected by water molecules interference, Raman spectroscopy is more suitable for the detection of biomolecules such as proteins, genes, etc. However, due to the low signal intensity, it did not reach a level of practical use despite long research period.

In the continuous researches since the discovery of Surface-Enhanced Raman Scattering, researches regarding the SERS enhancement phenomenon using a variety of nanostructures (nanoparticles, nanoshells, or nanolines) have been reported after the Surface Enhanced Raman Scattering (SERS) which is capable of detection of the single molecular level of signal in the disordered aggregate of nanoparticles with fluorescent molecules adsorbed, was reported (science 1997, 275(5303), 1102; Phys rev lett 1997, 78(9), 1667). Mirkin and his team recently successfully achieved high sensitivity DNA analysis using gold nanoparticles combined with DNA to use the SERS phenomenon with high sensitivity in the development of bio-sensors, with detection limit of 20 fM (2002, science, 297, 1536). However, there has been little progress in the preparation methods for single-molecule SERS active substrates based on salt induced aggregation of silver (Ag) nanoparticles with the Raman active molecule (eg, Rhodamine 6G) since the initial study. It was reported that in the heterogeneous coagulated colloid, only a fraction (less than 1%) has single molecule SERS activity (J Phys Chem B 2002, 106(2), 311). Although randomly inhomogeneous (roughed) surface provides a large amount of interesting and essential data associated with SERS, such a strategy is essentially reproducible due to significant changes in enhancement by small surface morphological changes. Recently, Fang et al. reported the quantitative measurements of distribution of enhanced regions in SERS. The densest areas (EF>$10^9$) were reported as 64 areas out of total 1,000,000 areas, which contribute to 24% of the total SERS intensity (Science, 2008, 321, 388). If the structure in which the SERS signal can be maximized with the reproducibility can be obtained, it can be a very reliable ultra-sensitive biomolecule analysis method, and can be useful for in vivo imaging techniques as well as in vitro diagnostics.

However, in the previous SERS detection methods for the various analytes, the substrate and/or colloidal metal particles, such as aggregated silver nanoparticles, coated on the supporter were typically used, sometimes yielding SERS detection with increased sensitivity by $10^6$ to $10^8$ times, without being able to detect single-molecule of small analytes such as nucleotides. However, despite the advantages of SERS, the mechanism of SERS phenomenon are not only not fully understood, the preparation and control of well-defined nanostructures are also difficult, as well as many unsolved problems exist in terms of reproducibility and reliability arising from the changes in enhancement efficiency depending on the wavelength of the light used to measure the spectrum, and the polarization direction remains an unsolved problem for the application of the SERS phenomenon including the development and commercialization of nanobiosensors. Researchers for precise control of the SERS phenomenon are required to solve these problems by means of understanding the optical properties of well-defined nanostructures.

Heresupon, L. Brus et al. (JACS. 2002) reported in the case of dimer of metal particles, that a hot spot (interstitial field), which is a very strong electromagnetic field, is formed between two or more nanoparticles, resulting in SERS signal enhancement and SERS enhancement by hot spot is predicted as $10^{12}$ times according to theoretical electromagnetic calculations.

Thus, the enhanced sensitivity of Raman detection is not evidently homogeneous within colloidal particle aggregate, but depends on the presence of hot spots. However, the characteristics of the physical structure and distance range from nanoparticles, where enhanced sensitivity is achieved, of hot spots, and spatial correlation between the analytes to enhance the sensitivity and aggregate of nanoparticles have not been presented. In addition, the aggregated nanoparticles are inherently unstable in solution, and give an adverse effect on the reproducibility of the detection of single-particle analyte.

As far as the amplification of optical signal is concerned, characteristic amplified signal (eg, Raman, fluorescence, scattering, etc) of molecules emitting the optical signal located in the gap can be detected by the amplification of electromagnetic signals at the junction area outside two or more nanostructures. However, if surface-enhanced Raman scattering (SERS) is to be obtained using these structures, quantification of the signal, reproducibility of the results, ease and simplicity of synthesis, cost, and stability of the probe still remain the problems. In other words, if two or more nanoparticles are combined by a nanogap, the amplified optical signal detection is detectable, but simplicity of material synthesis, stability, reproducibility of the signal and quantification cannot be secured.

Therefore, the nanostructure which is capable of strong amplification of the signal is a single nanoparticle with a nanogap inside and, even though it has not been reported until now, it is expected that stable signal can be formed by placing various signal substances in the intra-nanogap.

Meanwhile, although synthesis and assembly of various nanostructures for DNA have been studied in-depth, there have been very few researches on other roles of DNA. Hereupon, the present inventors prepared single nanoparticle which includes core and shell with a nanogap formed between core and shell using DNA, away from the concept to form a nanogap using more than two nanoparticles. For the nanoparticle herein, especially when modifying the surface of the core by the DNA, part of the space between the core and the shell is connected by the nanobridge, and the nanogap can be adjusted to be formed between the core and the shell, the number and locations of Raman-active molecules can be easily adjusted by adjusting the nucleotide sequence of DNA, the synthesis thereof is simple, very high signal amplification effect is shown due to plasomonic coupling by intra-nanogap, and the problem of signal reproducibility and quantification, which is the crucial prerequisite to commercialization, is known to be overcome due to high reproducibility to complete the present invention.

The present inventors also identified the possibility to form a nanogap without nanobridge between core and shell by forming organic molecules (polymer, as one example, polymer layer with layer-by-layer structure of poly-allyl amine, poly-L-lysine, which is positively charged polymer, and negatively charged poly-styrene-sulfonate) which can combine with the surface of gold nanoparticle followed by forming the additional metal shell.

DISCLOSURE

Technical Problem

The present invention is to provide a novel nanoparticle, which can be used effectively for optical signal analysis based on very high amplification effect of electromagnetic signal by plasomonic coupling of nanogap formation inside thereof and high reproducibility, and which includes core and surrounding shell with nanogap formation between the same, which may or may not be connected by a nanobridge, and the method of synthesis thereof.

The present invention is also to provide the method for detecting the analyte using the above nanoparticle and the analyte detection kit including the above nanoparticle.

Technical Solution

Accordingly, the present invention provides a nanoparticle comprising a core, a shell surrounding the core, and a nanogap formed between the core and shell. The core and shell may or may not be connected by a nanobridge.

As used herein, the term "core" refers to a spherical or pseudo-spherical particle with a diameter of 1 nm to 900 nm, which is composed of the metal that shows surface plasmon resonance. Gold, silver or copper may be used as the metal that shows surface plasmon resonance.

As used herein, the term "shell" refers to a coating layer surrounding the core, which is composed of the metal that shows surface plasmon resonance. Thickness of the shell is 0.1 nm to 900 nm, and preferably 10 nm to 100 nm. The nanogap is formed between the shell and core, and therefore there is a space formed between the shell and core. Gold, silver or copper may be used as the metal that shows surface plasmon resonance.

As used herein, the term "nanogap" refers to the space formed between the core and shell. The thickness of nanogap is preferably 0.01 nm to 100 nm. The nanogap can separate the core and shell, which may not be in contact at all by the nanogap or may be in contact by nanobridge. Therefore, the term "nanogap" used herein doesn't necessarily mean the space that separate completely core and shell.

As used herein, the term "nanobridge" refers to a bridge in the nanogap, with a diameter of 0.5 nm to 20 nm, to connect the core and shell. The nanoparticle in the present invention may comprises the "nanogap with nanobridge" or "nanogap without nanobridge" between the core and shell.

Therefore, as the preferred aspect of the present invention, the present invention relates the nanoparticle selected from the group consisting of i) a nanoparticle which consists of gold core and silver shell and has nanogap formed between gold core and silver shell, ii) a nanoparticle which consists of silver core and gold shell and has nanogap formed between silver core and gold shell, iii) a nanoparticle which consists of gold core and gold shell and has nanogap formed between gold core and gold shell, iv) a nanoparticle which consists of silver core and silver shell and has nanogap formed between silver core and silver shell. The most preferable nanoparticle in the present invention is a nanoparticle which consists of gold core and gold shell and has nanogap formed between gold core and gold shell. It also is not limited by the shape of the particles that make up the core.

Specifically, the core and shell are in contact, if any, in some areas through nanobridge. In other words, if the shell is formed on the core, the nanogap is formed between the entire surface of the core and the shell, but, in some areas, some of the substances that form the shell may form the nanobridge inside and have the structure of contact with the core. The typical structures were represented in FIGS. 1 and 2a. As represented in FIG. 1 FIGS. 1 and 2a in the process of the formation of the shell, some can be formed toward the core, resulting in the formation of nanobridge. The number of nanobridge is not limited from one to the extent which is capable of forming a nanogap. The diameter is preferably 0.5 nm to 20 nm. The nanobridge can cause the structure of the core and shell to be more stably maintained, and can be one factor that further increases the SERS signal.

The nanoparticle according to the present invention, where the space is formed between the core and shell by the nanogap, which enables amplification of Raman signal, can be used for detection of amplified optical signal. Specifically, the reproducibility of the nanogap is very high and, when the Surface-enhanced Raman Scattering (SERS) signal is acquired, quantification of the signal, reproducibility of results, cost, ease and simplicity of synthesis, and stability of the probe can be dramatically improved.

In order to clarify the above, FIG. 1 is used as reference. While the widely used multimeric nanostructure (FIG. 1, left) has multiple point gaps for plasmon coupling and SERS, it had drawbacks of extremely small surface area and heterogeneous point gaps. In particular, it is very difficult, and virtually impossible, to synthesize specific nanostructure which has high reproducibility and emits quantitative SERS.

On the other hand, the nanoparticle with nanobridged nanogap according to the present prevention provides the static and homogeneous gap with large surface area (FIG. 1, right). In the single intra-gap structure such as, the entire surface of the core can be used for enhancing the SERS, and the location of the dye also can be positioned precisely inside the structure. Furthermore, in actual use, it can be synthesized simply with high synthetic yield. In addition, a nanobridge is formed in some areas where the core and shell are connected so that the structure of nanoparticle can be maintained more stably.

A nanogap in the present invention can be formed by combing the polymer on the core and forming the shell on the polymer-combined core. That is, the presence of polymer between the core and shell prevents complete contact between the same, resulting in the formation of nanogap of isolated space. An oligonucleotide or polymer used in layer-by-layer assembly methods be used as the polymer and will be described in more detail in the following.

If the oligonucleotide is used, it is characterized by attachment of the oligonucleotide to the surface of the core of the nanoparticle by electrostatic attraction or covalent bond. Specifically, the present invention characterizes in that the surface of core is modified by one terminus of the oligonucleotide and the portion of oligonucleotide is inserted into the shell.

As used herein, the term "oligonucleotide" is a polymer composed of a small number of nucleotides, generally refers to shortest chemically synthesizable nucleotide-chain, which plays an important role in preparation of the nanoparticle according to the present invention. Specifically, poly-adenine (poly A) of oligonucleotide is placed preferably on the surface of core, because when forming the shell around the core, the shell is not in complete contact with core by oligonucleotide, resulting in formation of nanogap. However, if citrate or BSPP (bis(p-sulfonatophenyl)phenyl-phosphane dehydrate), as an example, is used instead of oligonucleotide, nanogap cannot be formed.

In addition, the oligonucleotide modifying the surface of core can also act as the optical signal-modifying platform where optical signal substance such as Raman active molecule is located. That is, it is possible to position the optical signal substance such as Raman molecule on the surface of the core, in the nanogap or inside the shell, and control precisely the position and number thereof, by combing the optical signal substance such as Raman active molecule with the oligonucleotide.

The oligonucleotide can be attached to the surface of core through the linker compound which 3' terminus or 5' terminus is modified to. As used herein, the term "linker compound" refers to a compound which is connected to the 3' or 5' terminus of each oligonucleotide and which serves to attach the oligonucletide to the surface of the core particle. The method for crosslinking the nanoparticles through a linker compound are known in the art (Feldheim, The Electrochemical Society Interface, Fall, 2001, pp. 22-25). The linker compound comprises at its one end a surface-bound functional group which binds to the surface of the core particle. Preferably, the surface-bound functional group is a sulfur-containing group such as thiol or sulfhydryl (HS). Thus, the functional group may be a compound represented by RSH, an alcohol or phenol derivative in which a sulfur atom is present instead of an oxygen atom. Alternatively, the functional group may be a thiol ester or dithiol ester group respectively represented by RSSR' and RSR' or an amino group (—NH$_2$).

In the present invention, 3'-HS—(CH$_2$)$_3$-A$_{10}$-PEG$_{18}$-AAACTCTTTGCGCAC-5' is used as the example of oligonucleotides, but is not limited thereto.

If the polymer available for layer-by-layer assembly method is used, the surface of the core of the nanoparticle is coated with polymer and the shell is formed on the coated core with the formation of nanogap, without the formation of nanobridge. Polymer coating is possible by covalent bond or electrostatic attraction, and if the electrostatic attraction is applied, layer-by-layer assembly is possible. The "layer-by-layer assembly" refers to a method for manufacturing a multilayer by stacking the positively and negatively charged polymer electrolytes alternately. Therefore, it is possible a method of manufacturing a multilayer with positively and negatively charged polymer electrolyte, respectively, are alternately stacked. Therefore, only one layer or coating to minimize the thickness of the nanogap by coating with only one layer or to control the thickness of nanogap by adjusting by adjusting the number of multi-layers Any polymer material used in the "layer-by-layer assembly", without limitation, can be used and for example, positively charged polymer poly-allyl amine, and poly-L-lysine, etc., with the negatively charged poly-styrene-sulfonate can be used.

In addition, the nanoparticle according to the present invention is characterized in comprising signal substance inside the nanogap. In particular, the optical active molecule for measuring the Raman signal may be any, without limitation, molecule consisting of atoms selected from the group consisting of C, H, O, N, S and combinations thereof, and the metal ion, metal ion chelate, or gold nanoparticle may be used. Specifically, signal substances used in the present invention have a broad concept that encompasses fluorescent organic molecules, non-fluorescent organic molecules, inorganic nanoparticles, and Raman active molecules, may include any markers, without limitation, with capability of color-development, and are desirably the Raman-active molecules. As used herein, the term "Raman-active molecule" refers to a substance which, when the nanoparticle in the present invention is attached to one or more analytes, facilitates the detection and measurement of the analyte by Raman detection device. Raman-active molecule used in Raman spectroscopy includes organic atom or molecule, or inorganic atom or molecules, etc. Specifically, the Raman-active molecule includes, but is not limited to, FAM (Fluorescein), Dabcyl (4-((4-(dimethylamino)phenyl)azo)benzoic Acid, Succinimidyl Ester), TRITC (tetramethyl rhodamine-5-isothiocyanate), MGITC (malachite green isothiocyanate), XRITC (X-rhodamine-5-isothiocyanate), DTDC (3,3-diethylthiadicarbocyanine iodide), TRIT (tetramethyl rhodamine isothiol), NBD (7-nitrobenz-2-1,3-diazol), phthalic acid, terephthalic acid, isophthalic acid, para-aminobenzoic acid, erythrocin, biotin, digoxigenin, 5-carboxy-4',5'-dichloro-2',7'-dimethoxy, fluorescein, 5-carboxy-2',4',5',7'-tetrachlorofluorescein, 5-carboxyfluorescein, 5-carboxyrhodamine, 6-carboxyrhodamine, 6-carboxytetramethyl amino phthalocyanine, azomethine, cyanine (Cy3, Cy3.5, Cy5), xanthine, succinylfluorescein, aminoacridine, quantum dot, carbon allotrope, cyanide, thiol, chlorine, bromine, methyl, phosphor or sulfur, must represent a distinct Raman spectrum and be able to be combined with, and specifically, related to the different type of analyte. Raman-active molecule is desirably the molecule which represents higher Raman signal intensity in resonance with wavelength of excitation laser used in Raman analysis.

The signal substance herein, which can be comprised in the nanogap, can be placed in the intra-nanogap by being attached on the oligonucleotide by covalent bound or electrostatic attraction, or Raman active molecule can be combined on the surface of the core particle by covalent bond or electrostatic attraction, regardless of the oligonucleotide. If the oligonucleotide is modified by the Raman-active molecule, the location of the Raman-active molecules is characteristically adjustable. That is, if the Raman-active molecule is attached in a position close to the terminus of oligonucleotide which is attached on the core, the Raman-active molecule can be positioned close to core in the nanoparticle, and can be positioned in the nanogap by adjustment. For example, the Raman signal can vary depending on the position of the Raman-active molecules, and if the Raman-active molecule is located in intra-gap, the strongest Raman signal with high uniformity and reproducibility can be detected.

If the Raman active molecule is combined on the surface of the core, regardless of the oligonucleotide, the combined weight of the Raman active molecule can be maximized.

Total diameter of the nanoparticle according to the present invention is preferably 1 nm to 990 nm, and preferably 20 nm to 500 nm.

In addition, a nanoparticle or shell can be formed on the nanoparticle according to the present invention, which enables formation of nanoparticle which has multiple layers of shell inside by repeating the above preparation method of the nanogap and shell.

The surface of the shell of the nanoparticle according to the present invention also can be combined with various substances, yielding improvement of the characteristics of nanoparticle. For example, if the nanoparticle is used in the living body, the surface can be modified by biocompatible polymers. In addition, biomolecule can be functionalized on the surface of the shell of the nanoparticle according to the present invention. If the surface of the nanoparticle according to the present invention is functionalized by biomolecule, nanoparticle can be combined only to the specific target, resulting in further improvement of analysis capability using the nanoparticle. Examples of biomolecules functionalized to nanoparticle may be antibody, antibody fragment, genetically engineered antibody, single-chain antibody, protein receptor, binding protein, enzyme, protein inhibitor, lectin, cell adhesion protein, oligonucleotide, polynucleotide, nucleic acid, or aptamer.

The present invention also provides the method for preparation of the nanoparticle comprising a core, a shell surrounding the core, and a nanogap formed between the core and shell, comprising modifying the core by an oligonucleotide; and forming the shell on the oligonucleotide modified core.

The first step is for modifying the core by the oligonucleotide and can be performed using a method known in the art according to the publicly known literature. In the examples of the present invention, the reference 'S. J. Hurst, A. K. R. Lytton-Jean, C. A. Mirkin, Anal. Chem. 78, 8313 (2006)' was referred to.

The second step is for forming a shell, by reacting the metal precursor (for example, gold precursor HAuCl$_4$), reducing agent (NH$_2$OH—HCl), and poly-N-vinyl-2-pyrrolidone (PVP) using a phosphate-buffered solution.

According to the above method for preparing a nanoparticle, the nanoparticle of the core-nanogap-shell can be prepared with high yield (of at least approximately 95%), and in particular with very good reproducibility of the nanogap. In addition, if oligonucleotide combined signal substances is used in the first step, nanoparticle including signal substance can be prepared, and the location and number of signal substances in the nanoparticle can be easily adjusted accordingly.

Further, the present invention also provides the method for preparation of the nanoparticle comprising a core, a shell surrounding the core, and a nanogap formed between the core and shell, comprising coating the core with a polymer; and forming the shell on the coated core. The coating of polymer can be carried out by layer-by-layer assembly, and any material used in the "layer-by-layer assembly", without limitation, can be used and for example, positively charged polymer poly-allyl amine, and poly-L-lysine, etc., with the negatively charged poly-styrene-sulfonate can be used.

Further, the present invention also provides the method for detecting an analyte, comprising synthesizing the nanoparticle of the present invention; functionalizing the surface of the shell of the nanoparticle with a bio-molecule capable of detecting an analyte; exposing the nanoparticle to a sample containing at least one analyte; and detecting and identifying the analyte by laser excitation and Raman spectroscopy.

Examples of the analyte herein may be amino acids, peptides, polypeptides, proteins, glycoproteins, lipoprotein, nucleoside, nucleotide, oligonucleotide, nucleic acids, sugars, carbohydrates, oligosaccharides, polysaccharides, fatty acids, lipids, hormones, metabolite, cytokines, chemokines, receptors, neurotransmitters, antigens, allergens, antibodies, substrates, metabolites, cofactors, inhibitors, drugs, pharmaceutical substance, nutrients, prions, toxins, poison, explosives, pesticides, chemical warfare agents, bio-hazard substance, radioisotope, vitamin, heterocyclic aromatic compounds, carcinogens, mutagenic agent, narcotics, amphetamines, barbiturate, hallucinogens, waste or pollutants. In addition, if the analyte is nucleic acid, the nucleic acid herein can be gene, viral RNA and DNA, bacterial DNA, fungal DNA, mammalian DNA, cDNA, mRNA, RNA and DNA fragments, oligonucleotide, synthetic oligonucleotide, modified oligonucleotide, single-strand and double-strand nucleic acid, natural and synthetic nucleic acids.

Examples of biomolecules functionalized to nanoparticle herein may be antibody, antibody fragment, genetically engineered antibody, single-chain antibody, protein receptor, binding protein, enzyme, protein inhibitor, lectin, cell adhesion protein, oligonucleotide, polynucleotide, nucleic acid, or aptamer. Functionalization can be carried out by attaching biomolecules on the surface of nanoparticle by electrostatic attraction, directly or through linker, and the method of functionalization is not specifically limited.

Preferably, the analyte in the present invention can be detected or identified with publicly known Raman spectroscopy, and preferably with Surface Enhanced Raman Scattering (SERS), Surface Enhanced Resonance Raman Spectroscopy (SERRS), and hyper-Raman and/or Coherent Anti-Stokes Raman spectroscopy (CARS).

As used herein, the term "Surface Enhanced Raman Scattering (SERS)" refers to a the spectroscopy using the phenomenon which is a type of Raman scattering, whose Raman intensity is increased by more than $10^6$ to $10^8$ times compared with general Raman intensity, occurred when adsorbed on roughed surface of specific metal or located within a distance of several hundred nanometers. The term "Surface Enhanced Resonance Raman Spectroscopy (SERRS)" refers to a spectroscopy using resonance of laser excitation wavelength with the absorbate on the SERS active surface. The term "Coherent Anti-Stokes Raman Spectroscopy (CARS)" refers to the spectroscopy measuring the spectrum of anti Stokes radiation obtained by the combination of two, fixed and variable, incident laser light onto the Raman-active medium.

In the examples herein, the Raman active substrate can be operationally combined with one or more Raman detection units. Several methods for detecting an analyte by Raman spectroscopy is known in the art (eg, U.S. Pat. No. 6,002,471, U.S. Pat. No. 6,040,191, U.S. Pat. No. 6,149,868, U.S. Pat. No. 6,174,677, U.S. Pat. No. 6,313,914). Sensitivity of Raman detection for SERS is enhanced by more than $10^6$ times for the molecules absorbed on the rough metallic surface, for example, surface of silver, gold, platinum, copper or aluminum.

Non-limiting example of Raman detection device is disclosed in U.S. Pat. No. 6,002,471. Excitation beam is generated by frequency doubled Nd:YAG laser at a wavelength of 532 nm or frequency doubled Ti:Sapphire laser at a wavelength of 365 nm. Pulsed laser beam or continuous laser beam can be used. Excitation beam passes through confocal optics and microscope lens, and is focused onto Raman active substrate containing one or more analytes. Analysis of water Raman emission light from the analyte was collected by the microscope lens and a confocal optics and combined with monochrometer for spectral separation. Confocal optics includes a combination of dichroic filter for reducing the background signal, cutoff filter, confocal pinhole, objective lens and mirror. Standard full field optical device as well as confocal optics can be used. Raman emission signal is detected by the Raman detector that includes avalanche photodiode which interfaces with the computer to count and digitize the signal.

Another example of detection device is disclosed in U.S. Pat. No. 5,306,403, which is a double grating spectrometer (Spex Model 1403) equipped with gallium-arsenide photomultiplier (RCA Model C31034 or Burle Industries Model C3103402) operating as a single-photon counting method. Excitation source includes the 514.5 nm line argon-ion laser (SpectraPhysics, model 166) and 647.1 nm line of krypton-ion laser (Innova 70, incoherent).

Other excitation sources include nitrogen laser at 337 nm (Laser Science Inc.) and helium-cadmium laser at 325 nm (Liconox) (U.S. Pat. No. 6,174,677), light-emitting diode, Nd:YLF laser, and/or various ion lasers and/or dye laser. Excitation beam can be refined spectrally by band-pass filter (Corion) and focused on Raman active substrate using 6× objective lens (Newport, Model L6X). Objective lens can be used to excite an analyte by using holographic beam splitter (Kaiser Optical Systems, Inc., Model HB 647-26N18), collect Raman signal, and polarize the emitted Raman signal perpendicular to excitation beam. Holographic notch filter (Kaiser Optical Systems, Inc.) can be used to reduce Rayleigh scattering radiation. Other Raman detectors include ISA HR-320 spectrometer equipped with high sensitivity red enhanced charge-coupled device (RE-ICCD) detection system (Princeton Instruments). Other types of detectors such as Fourier transform spectrometer (based on the Michelson interferometer), charge injection device, photodiode array, InGaAs detector, electron multiplication CCD, high sensitivity CCD and/or phototransistor arrays can be used.

Any well-known suitable form or configuration of Raman spectroscopy or related technique may be used for detecting an analyte. Examples include normal Raman scattering, resonance Raman scattering, surface enhanced Raman scattering, surface enhanced resonance Raman scattering, coherent anti-Stokes Raman spectroscopy, Molecular Optical Laser Examiner (MOLE), Raman microprobing or Raman microscopy, confocal Raman microspectrometer, 3-D or scanning Raman, Raman saturation spectroscopy, time resolution differential resonance Raman, Raman dissociation spectroscopy, or UV-Raman microscopy, but are limited thereto.

In a specific example of the present invention, Raman detection device can be operationally linked with computer. Data from detection device is processed by processor and stored in a main memory device. Data in emission profile for the standard analyte also can be stored in a main memory device or ROM. Processor can compare emission spectra from the analytes on the Raman active substrate and identify the type of analyte in the sample. Processor can analyze the data from detection device and determine the identity and/or concentration of various analytes. Differently configured computer may be used to serve different purposes. Therefore, the structure of the system may be different in different example of the present invention. After being collected, data are typically transferred to analyzing process. In order to make the analyzing process easy, data obtained from the detection device are typically analyzed by digital computer. Typically, the computer is programmed appropriately to receive and store the data from detection device as well as analyze and report the collected data.

The present invention also provides the analyte detection kit including nanoparticle according to the present invention. The detection kit will include tools and reagents that are commonly used in the art. These tools/reagents may include, but is not limited to, a suitable carrier, marker which can generate a detectable, solvent, detergent, buffer, and stabilizer. If the marker is an enzyme, it may include substrate and chain stopper which are capable of measuring enzyme activity. Suitable carrier may include, but not limited to, the soluble substrate, for example, physiologically acceptable buffer known in the art, which may be, for example, PBS, insoluble carrier, whose example may be polystyrene, polyethylene, polypropylene, polyester, polyacrylonitrile, fluorine resin, cross-linked dextran, polysaccharides, polymers such as magnetic particulate which is metal plated latex, other paper, glass, metal, agarose, and combinations thereof.

The nanoparticle according to the present invention may replace the nanoparticle used in conventional molecular diagnostic chip for detection or conventional imaging diagnosis. The nanoparticle according to the present invention can be applied to molecular diagnostic chip such as DNA chip and protein chips. The analytes to be detected may be gene, viral RNA and DNA, bacterial DNA, fungal DNA, mammalian DNA, cDNA, mRNA, RNA, DNA fragment, oligonucleotide, synthetic oligonucleotide, modified oligonucleotide, single-strand and double-strand nucleic acid, natural and synthetic nucleic acids, amino acids, peptides, polypeptides, proteins, glycoproteins, lipoprotein, nucleoside, nucleotide, oligonucleotide, nucleic acids, sugars, carbohydrates, oligosaccharides, polysaccharides, fatty acids, lipids, hormones, metabolite, cytokines, chemokines, receptors, neurotransmitters, antigens, allergens, antibodies, substrates, metabolites, cofactors, inhibitors, drugs, pharmaceutical substance, nutrients, prions, toxins, poison, explosives, pesticides, chemical warfare agents, bio-hazard substance, radioisotope, vitamin, heterocyclic aromatic compounds, carcinogens, mutagenic agent, narcotics, amphetamines, barbiturate, hallucinogens, waste or pollutants.

The nanoparticle according to the present invention may be highly applicable to the detection of analyte such as DNA and protein related to the onset and progress of particular diseases, and applicable to molecular diagnostic technique and molecular imaging field, such as large-scale genome sequence analysis, Single Nucleotide Polymorphism (SNP) detection, sequence comparison, genotype-specific analysis, care and drug development.

In addition, on the surface of nanoparticle according to the present invention, the substance which indicates other signal can be included inside or outside of the nanoparticle. For example, the CT contrast agents, MRI contrast agents, optical contrast agents, ultrasound contrast agents, or a combination of these substances can be included additionally, featuring that Raman analysis using nanoparticle can be performed along with CT, MRI, optical or ultrasonic analysis at the same time accordingly.

In addition, the nanoparticle according to the present invention may include genes, antibodies or drugs, and accordingly can be used in the treatment of disease as drug carrier.

Advantageous Effect

The nanostructure of nanogap particle has a large surface area and provides the nanogap of high reproducibility and uniform thickness. Accordingly, the entire surface of the core can be used for enhancing the SERS, and the location of the dye also can be positioned precisely inside the nanogap. Furthermore, in actual use, it can be synthesized simply with high synthetic yield. Therefore, very high signal amplification effect is shown, and the problem of signal reproducibility and quantification, which is the crucial prerequisite to the commercialization, can be overcome due to high reproducibility.

DESCRIPTION OF FIGURES

FIGS. 2a, 2b, and 2c represent a method for preparing a nanoparticle according to the example of the present invention and analysis result thereof. FIG. 2a represents the process of formation of shell, FIG. 2b visible light spectrum graph of intermediate 1, 2, 3 and nanoparticle (4, 5), FIG. 2c TEM image of intermediate 1, 2, 3 and nanoparticle (4, 5), and FIG. 2c the result of atom-mapping of nanoparticle, respectively.

FIG. 9a represents calculation result of electromagnetic field distribution of NNP (it is assumed that gap is full of DNA and Raman reporter molecules and surroundings of the particle is filled with water), FIG. 9b calculation result of electromagnetic distribution of gold-gold core-gap-shell nanoparticle surrounded by silica of the same size as NNP, FIG. 9c comparison result of electromagnetic distribution along the center line at 632.8 nm, and FIG. 9d dependence of NNP on the incident beam, respectively.

FIG. 10A represents the Raman signal at different wavelengths, FIG. 10B the Raman signal of the nanoparticle with a dye located in the nanogap, FIG. 10C the Raman signal of the nanoparticle with a dye located inside the shell, and FIG. 10D the Raman signal of the nanoparticle with a dye located outside the shell, respectively.

FIG. 12a represents the result of Raman signal according to the number of dyes, FIG. 12b the intensity of Raman signal according to the number of dyes, and FIG. 12c the intensity of Raman signal according to the thickness of shell, respectively.

FIG. 14a represents the intensity of Raman signal for the nanoparticle with Cy3 and FIG. 14b represents the intensity of Raman signal for the nanoparticle with 4,4'-dipyridyl.

FIG. 15a to FIG. 15e represent an AFM image in tapping-mode of nanoparticle.

PREFERABLE MODE FOR INVENTION

Figure 1:
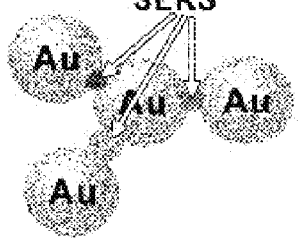
FIG. 1 represents a conventional multimetric nanostructure and NNP nanostructure according to the example of the present invention.
Figure 1:
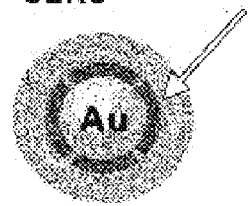

The present invention is described in more details through providing examples as below. However, these examples are merely meant to illustrate, but in no way to limit, the claimed invention.

Material Used

Gold nanoparticle was purchased from Ted Pella (Redding, Calif., USA). All other chemical materials (HAuCl$_4$.3H$_2$O, polyvinylpyrrolidone (K value: 29-32), NH$_2$OH.HCl, Dithiothreitol, BSPP) were purchased from Sigma-Aldrich (St. Louis, Mo., USA) and used as received without further purification. HPLC-purified dye-coded thiolated oligonucleotides were purchased from IDT Inc. (Coralville, Iowa, USA) and reduced by using dithiothreitol (DTT, 0.1 M) in a phosphate buffer (0.17 M, pH=8.0). The reduced oligonucleotides were then purified through a desalting NAP-5 column (Sephadex G-25 medium, DNA grade). NANO pure H$_2$O (>18.0 MΩ), purified using a Milli-Q water purification system, was used for all experiments. The formvar/carbon coated copper grid (Ted Pella, Inc. Redding, Calif., USA) and HR-TEM (JEM-3010, Japan, 300 kV) equipped with EDS unit (Link oxford ISIS 310) was used for TEM analysis.

Optical Calculation for the NNP and Silica-Insulated Nanoparticle

To understand correlation between electromagnetic wave and bridged Au core-gap-shell, 3D finite element model was studied using commercially available FEM software COS-MOL which is capable of calculating the time-harmonic Maxwell equation on the given boundary condition. Linearly(x) polarized wave (λ=632 nm) was incident on the bridged Au core-gap-shell particle. Empirical dielectric constant of gold by Johnson and Christy was used with interpolation ((1) P. B. Johnson, R. W. Christy, Phys. Rev. B. 6, 4370-4379 (1972); (2) P. G. Etchegoin, E. C. Le Ru, M. Meyer, J. Chem. Phys. 125, 164705 (2006)).

Relative permeability of gold is $\mu_r=1$, and complex refractive index was calculated as $\eta_{Au}(\lambda)=\sqrt{\varepsilon_{Au}(\lambda)}=\eta+ik$ Dielectric constants of water, air, and silica are $e_{water}=1.33^2$, $e_{air}=1$, $e_{SIO2}=1.46^2$, respectively. Effective dielectric constant of mixture of air and DNA in the gap area was determined by Maxwell-Garnett equation:

$$\varepsilon_{eff} = \varepsilon_0 \frac{\varepsilon_{DNA}(1+2\phi) + 2\varepsilon_0(1-\phi)}{\varepsilon_{DNA}(1-\phi) + \varepsilon_0(2+\phi)}$$

wherein, $e_{eff}$ is effective dielectric constant of the mixture of water (or air) and DNA, $e_0$ is dielectric constant of water (or air), $e_{DNA}$ is dielectric constant of DNA (G. Rong, A. Najmaie, J. E. Sipe, S. M. Weiss, Biosensors and Bioelectronics 23, 1572-1576 (2008)) ($e_{DNA} \sim 1.5$), and f represents a volume fraction of DNA in the gap area. 300 nucleotides were assumed to be present in the gap area and a volume fraction of DNA in the gap area is about 0.0048 accordingly.

Nano-Raman Experimental Setup

Raman spectrum was measured with a nano-Raman spectroscope (Axiovert 200, Zeiss) equipped with an inverted optical microscope and independently adjustable piezoelectric x, y sample scanner (Physik Instrumente). Argon ion laser (Melles Griot, USA) of 514.5 nm, He—Ne laser (JDSU, USA) of 632.8 nm, and diode laser (B&W TEK INC.) of 785 nm were used as excitation source coupled with single-mode optical fiber. Excitation laser beam of 50 nW to 1 mW was reflected by dichroic mirror (Chroma Technology Corp.) on oil-immersion microscope objective (×100, 1.3 numerical aperture; ×50, 0.5 numerical aperture; Zeiss), focused on the diffraction-limited spot (<300 nm and <3 μm for ×100 and ×50 objective lens, respectively, when laser of 632.8 nm is used) on the upper surface of cover-glass slip. AFM (Bioscope, Digital Instruments, Veeco Metrology Group) equipped with a nanoscope IV controller was installed on the micro-mechanical stage. Background Raman signal was collected by CCD (charge-coupled device) which was frozen by liquid nitrogen (−125° C.). Tapping mode on closed-loop piezoelectric flexure sample stage and closed-loop AFM scanner were used in order to relate Raman or Rayleigh scattering signal to AFM topographical image of overlap precision of <50 nm and sample image. Focus of laser is coincided with AFM tip so to disperse symmetrically to AFM tip. Scattering spectrum was measured at the range of 500~2000 cm-1 single and at 10 seconds. All data was baseline-corrected by removing background signal from Si. For all solution used in Raman analysis, 384 well optical bottom plate (Nunc™, New York, USA) was used. In AFM-correlated nanoRaman analysis, Ploy-L-lysine coated cover glass (piranha-etched) was used. In one of the preferred embodiments, the DNA sequences include the following sequences:

AAAAAAAAAA (SEQ ID No. 1) shorthand notation as the A$_{10}$ spacer AAACTCTTTGCGCCAC (SEQ ID No. 2).

Example 1

Preparation of Core-Gap-Shell Nanoparticle

Single NNP nanoparticle with intra-nanogap was prepared according to the method in the following, using DNA strand as Raman-dye modification platform with ability to adjust the location very precisely. The method is also represented schematically in FIG. 2a.

As a typical preparation method, DNA modified gold nanoparticle (20 nm particle; DNA sequence: 3'-HS—$(CH_2)_3$-$A_{10}$-$PEG_{18}$-AAACTCTTTGCGCAC-5') (i.e., 20 nm particle; DNA sequence: 3'-HS—$(CH_2)_3$-SEQ ID No 1-$PEG_{18}$-SEQ ID No 2-5') was prepared according to the literature 'S. J. Hurst, A. K. R. Lytton-Jean, C. A. Mirkin, Anal. Chem. 78, 8313 (2006)'. In order to form a shell (Au) surrounding a core of DNA modified gold nanoparticle, the DNA modified gold nanoparticle was reacted with gold precursor ($HAuCl_4$), reducing agent ($NH_2OH$—HCl) and 1% poly-N-vinyl-2-pyrrolidone (PVP; MW 40,000) in phosphate-buffered solution (0.3 M NaCl; 10 mM PB; pH 7.4) and was vortexed for 30 minutes at room temperature. In order to determine the change in the form of nanoparticle according to the process of the formation of the shell, the amounts of gold precursor ($HAuCl_4$) and reducing agent ($NH_2OH$—HCl) were adjusted on the basis of amount of seed (DNA modified gold nanoparticle, 1 nM).

Concretely, DNA modified gold nanoparticle solution (100 μL; 1 nM in 0.3M PBS) was mixed with 1% PVP solution of 50 μL. The resultant solution was mixed with hydroxylamine hydrochloride solution (10 mM) of 1.5 μL, 5.2 μL, 10.3 μL or 30.4 μL and mixed with chloroauric acid solution (5 mM) of 1.5 μL, 5.2 μL, 10.3 μL or 30.4 μL, respectively. A variety of nanostructures were formed according to the amount of reactant (FIGS. 2b and 2c; intermediate (1, 2 and 3) and product (4, 5)). The pattern of nanostructure prepared for each solution was observed as in FIG. 3.

Figure 2B:
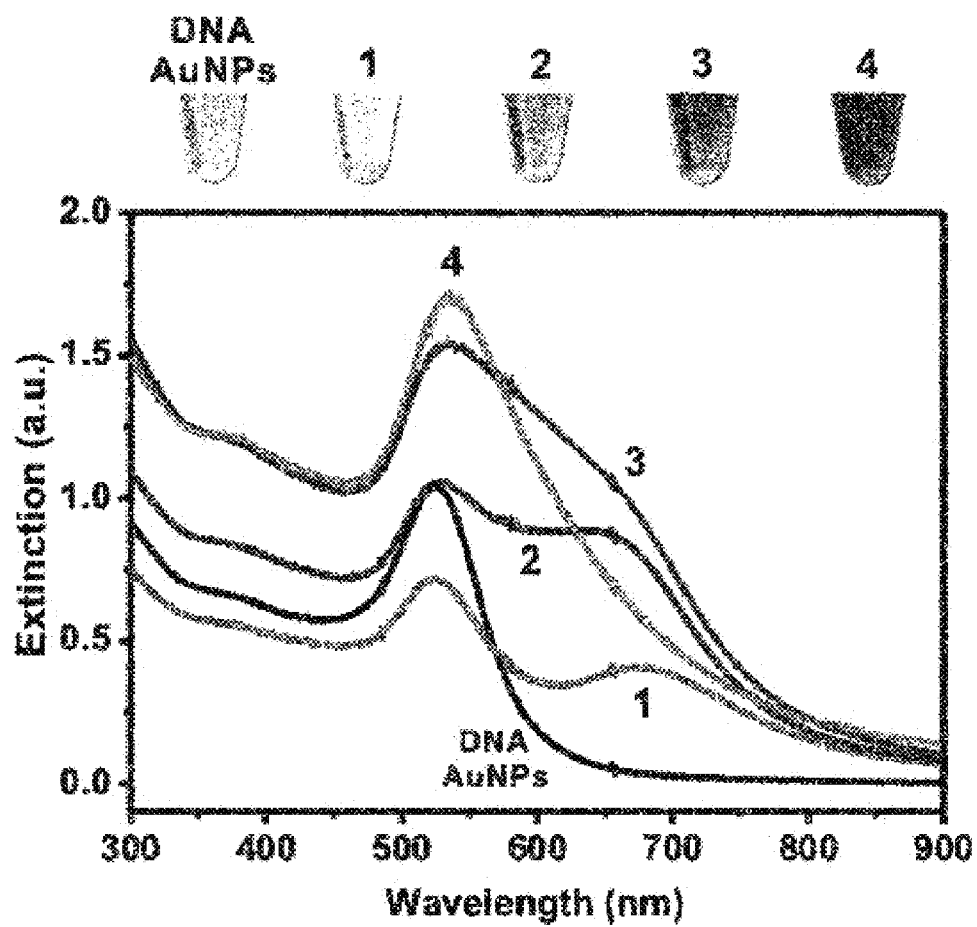
Figure 2C:
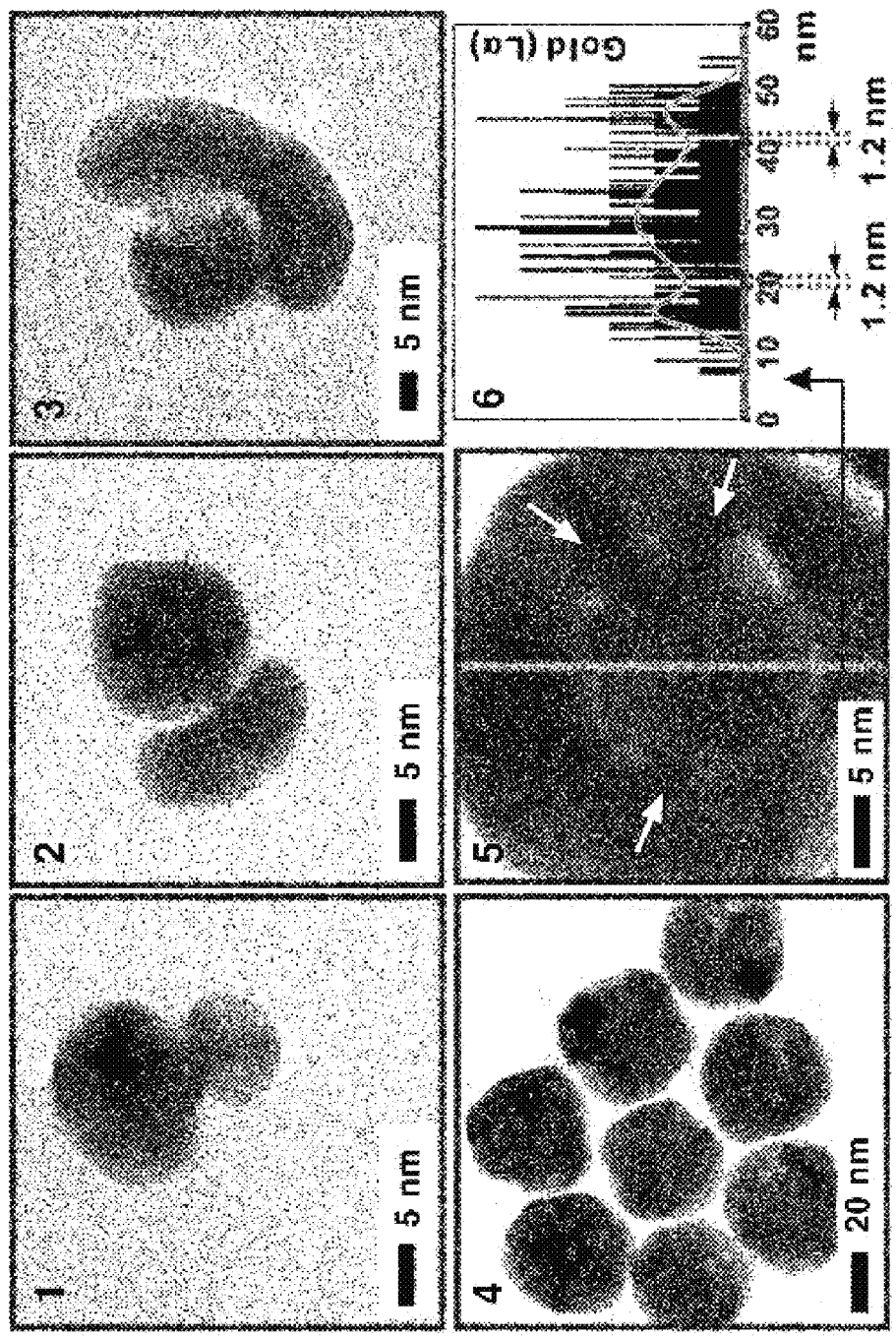

In the preparation process, the color of particle solution changed from pink (DNA modified gold nanoparticle) to pale pink (intermediate 1; budding structures), blue (intermediate 2), purple (intermediate 3; intermediate shell structure), and finally to red-wine color (NNP structure), as represented in FIG. 2b, which coincide with UV-Vis spectra and HR-TEM represented in FIGS. 2b and 2c, respectively.

Figure 3:
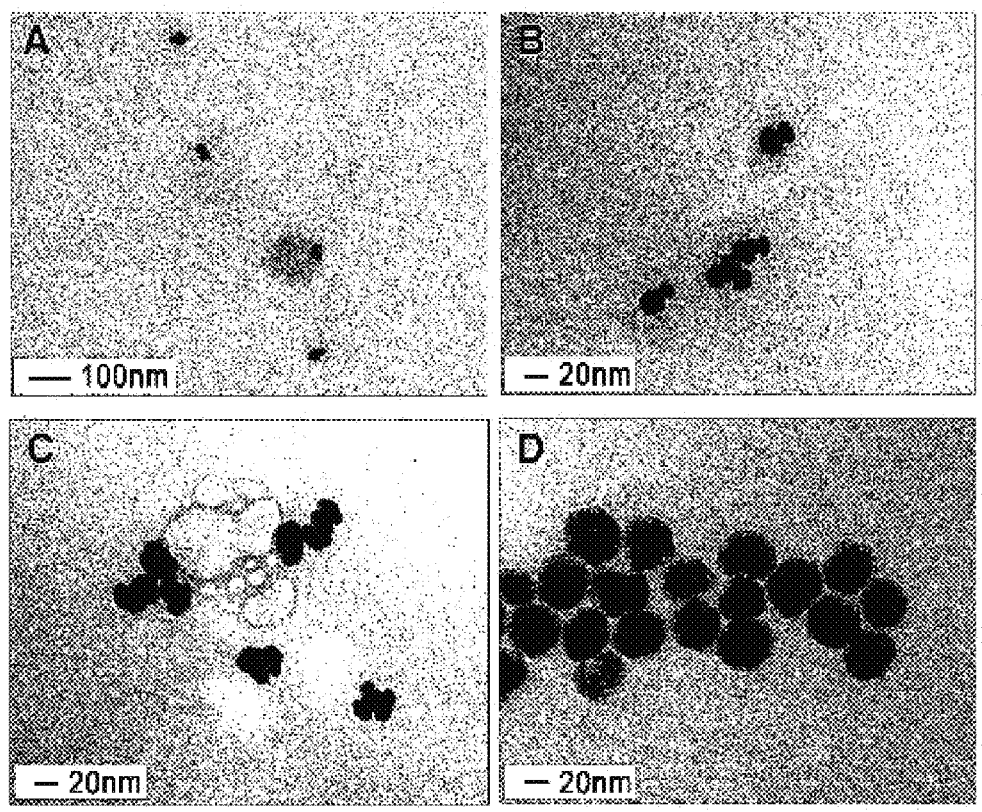
FIGS. 3a, 3b, 3c, and 3d represent a TEM image observed according to the concentration of each solution used in the process of preparing the nanoparticle according to the example of the present invention.
Figure 4:
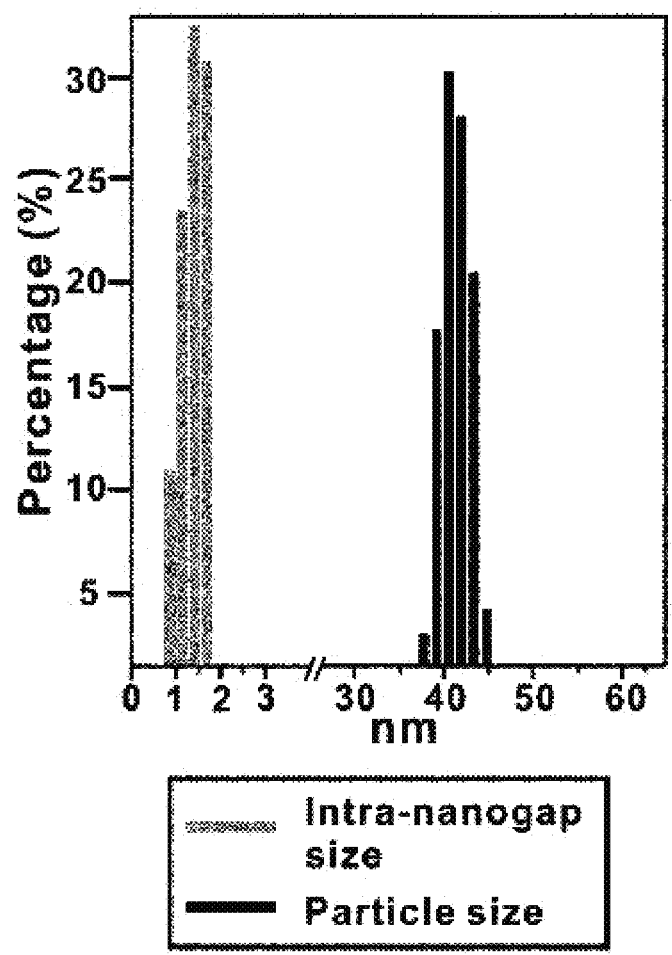
FIG. 4 represents size of NNP particles (200) and size distribution of intra-nanogap prepared according to the example of the present invention.

Interestingly, as the more reactant was added, the smaller budding sphere began to appear and was formed sideways on DNA-modified gold surface. Shell-like structure was gradually formed, and nanogap was observed in the process (FIG. 2b, FIG. 2c, and FIG. 3). UV-Vis spectrum represents that the color change of the solution is closely related to HR-TEM images (FIG. 2b). UV-Vis spectrum of the intermediate 1 (FIG. 2b 1) indicates that plasmonic resonance peak of approximately 680 nm is due to transverse mode along the long axis of the synthesized budding structures (FIG. 2c 1) and such peaks gradually disappeared as the shell is formed (FIG. 2b 4). For the final product (Au-NNPs (nanoparticle of gold core-nanobridged nanogap-gold shell structure); core of about 20 nm, gap of about 1.2 nm, and shell of about 11 nm), plasmon resonance peaks were close to the template particles (about 520 nm for DNA modified gold nanoparticles (DNA-Au-NNPs)) with broader peak shape by perfect nanoshell structure (FIG. 2b 4), but UV absorbance is enhanced by more than 4 times compared with DNA-Au-NNPs (UV-spectrum in FIG. 2b) was obtained from the diluted solution by 2 times). Calculated extinction coefficient of the product is about $7.2 \times 10^9$ $M^{-1}cm^{-1}$.

Figure 5:
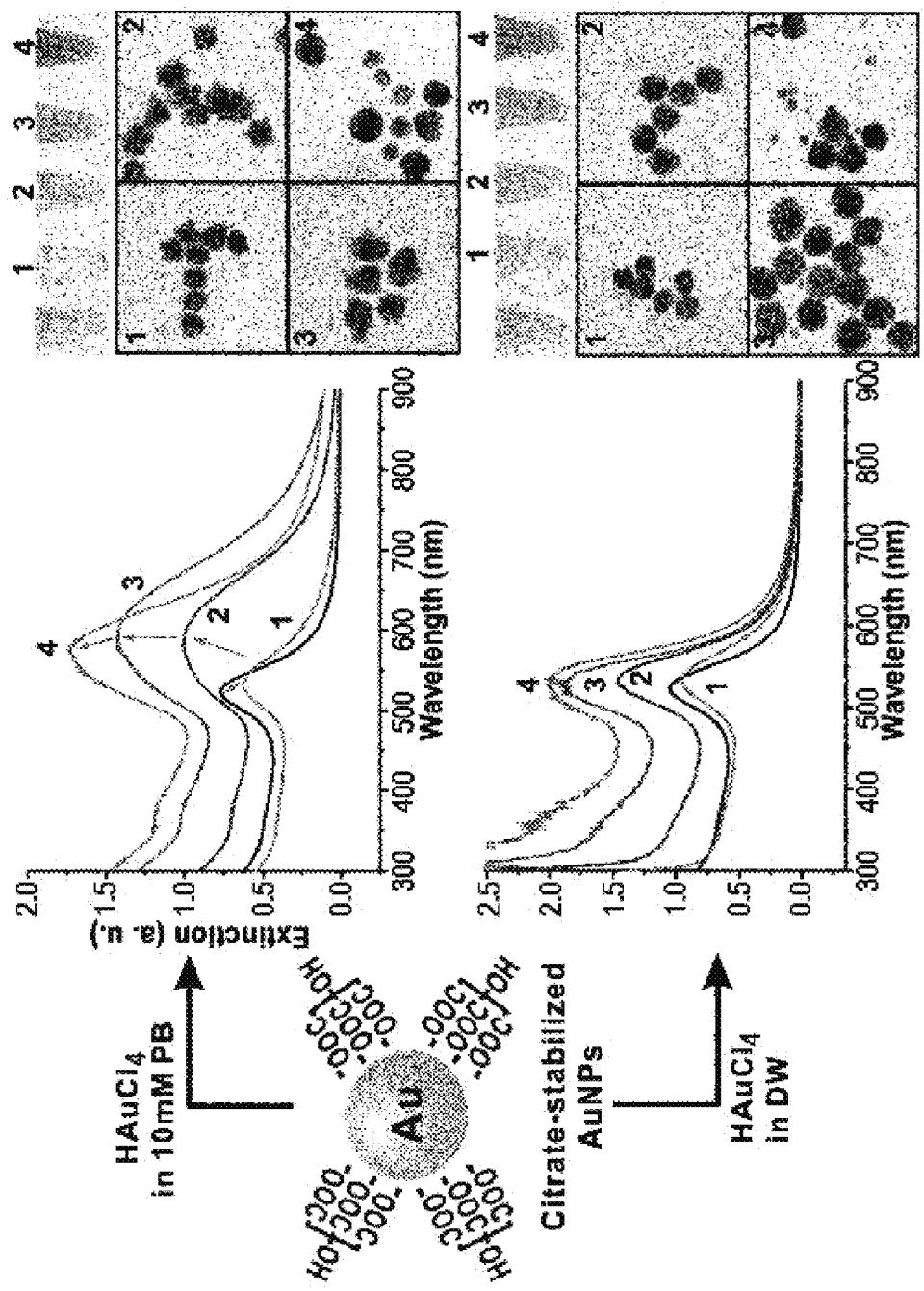
FIG. 5 represents visible light spectrum graph and TEM image of nanoparticle prepared using citrate-stabilized 20 nm gold nanoparticle as seed.
Figure 6:
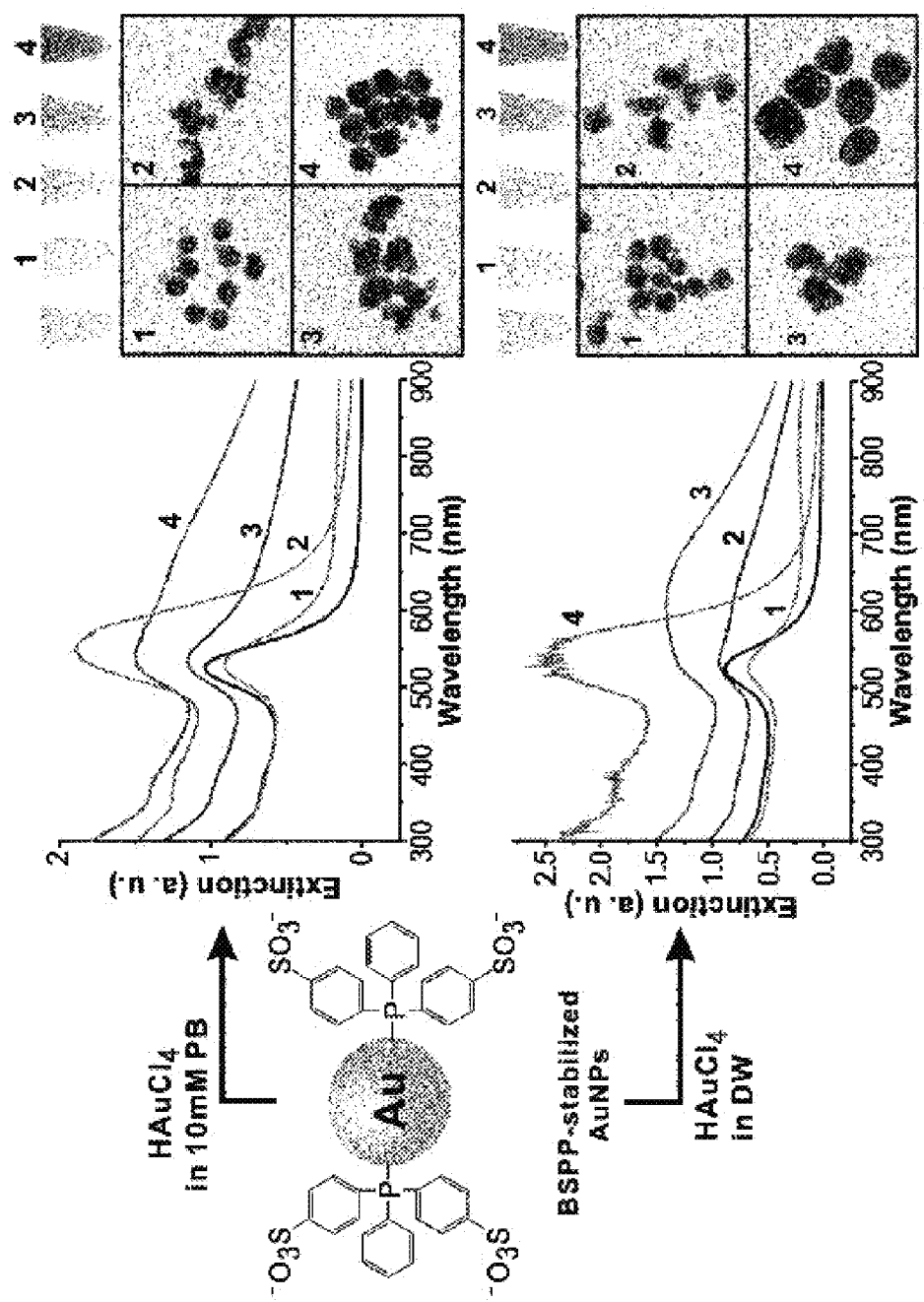
FIG. 6 represents visible light spectrum graph and TEM image of nanoparticle prepared using SPP (bis(p-sulfonatophenyl)phenylphosphane dehydrate) modified gold core.

Importantly, HRTEM image of intermediates 2, 3, and the final product (4, 5) indicates that nanobridge is formed by partial contact between shell and the surface of core, and nanobridged nanogap was formed on the surface of core (average gap size is approximately 1.2 nm; FIG. 2c 4, 5, 6). The final product (Au-NNPs) was prepared with high yield (approximately 95%) as a final product, and all particles has uniform intra-nanobridged nanogap as TEM image shown in FIGS. 2c 4 and 5. The average diameter measured by TEM image is 42±5 nm (FIG. 4). Element line mapping of Au—NNP shown in FIG. 2c 6 represents a reduced area of gold atoms (about 1.2 nm), which coincides with the nanogap observed in FIG. 2c 5. Prepared NNP in solution was a substantially stable for more than 6 months under atmospheric conditions (room temperature and 0.3 M PBS).

Comparative Example 1

Preparation of Surface Modified Nanoparticle by Substance Other than Oligonucleotide In order to understand the role of surface modified oligonucleotide, comparative example was prepared as follows.

Nanoparticle was prepared by the same method as in Example 1, except using citrate-stabilized 20 nm gold nanoparticle as seed, and 10 mM phosphate buffer or deionized water. Branched form or nanoshell was formed on the gold core without the formation of intra-nanogap (FIG. 5).

Nanoparticle was also prepared by the same method as in Example 1, except that BSPP (bis(p-sulfonatophenyl)phenylphosphane dehydrate) was modified on the surface of gold nanoparticle and the resultant BSPP modified gold nanoparticle was used as seed. In this case, the growth of shell is somewhat irregular and highly polydisperse nanostructure was prepared without the formation of intra-nanogap (FIG. 6).

For both cases, although the surface charges (the zeta potentials of citrate-gold nanoparticle and BSPP-gold nanoparticle are −35±3 mV and −45±3 mV, respectively) were not significantly different form that of DNA-AuNPs (−25±1 mV), the growth pattern of the shell was completely different.

Figure 7:
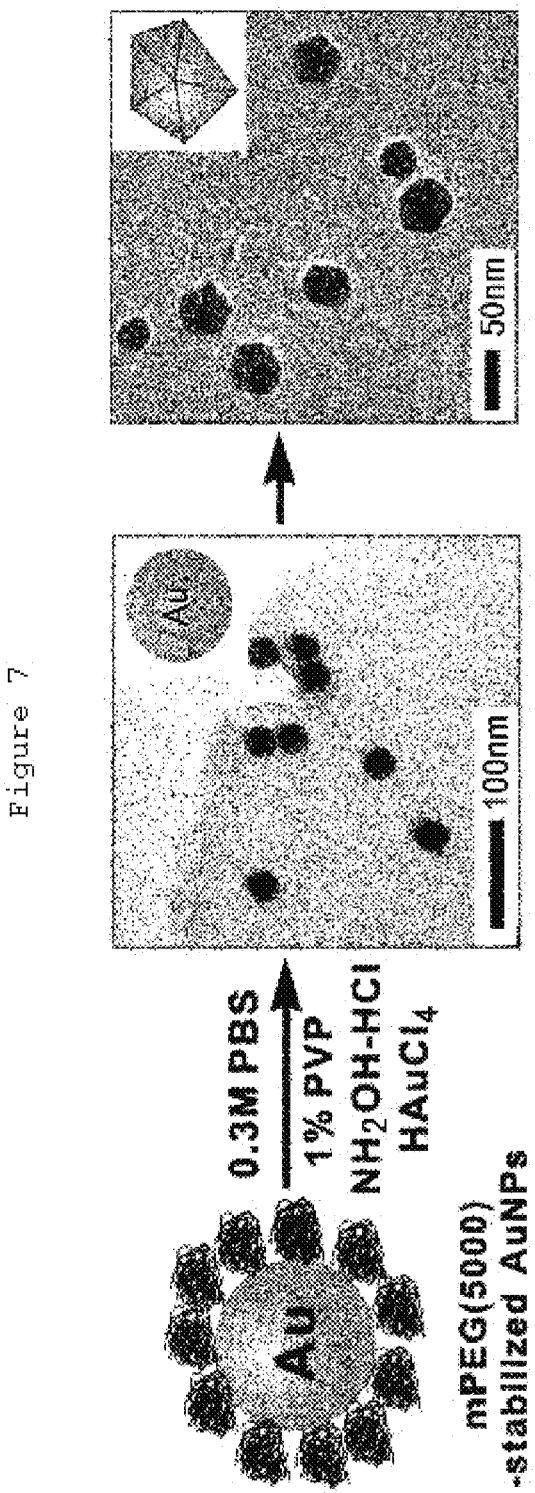
FIG. 7 represents TEM image of nanoparticle prepared using mPEG modified gold nanoparticle as seed.

Nanoparticle was also prepared by the same method as in Example 1, except using mPEG (molecular weight 5,000) thiol modified gold nanoparticle as seed. In this case, the nanoparticle of slightly distorted pentagonal or spherical structure was prepared without the formation of intra-nanogap (FIG. 7).

The results identified that DNA is very important in preparing a nanoparticle of core-nanogap-shell structure according to the present invention.

Comparative Example 2

Preparation of Nanoparticle Using T10 Spacer Instead of A10 Spacer

Figure 8:
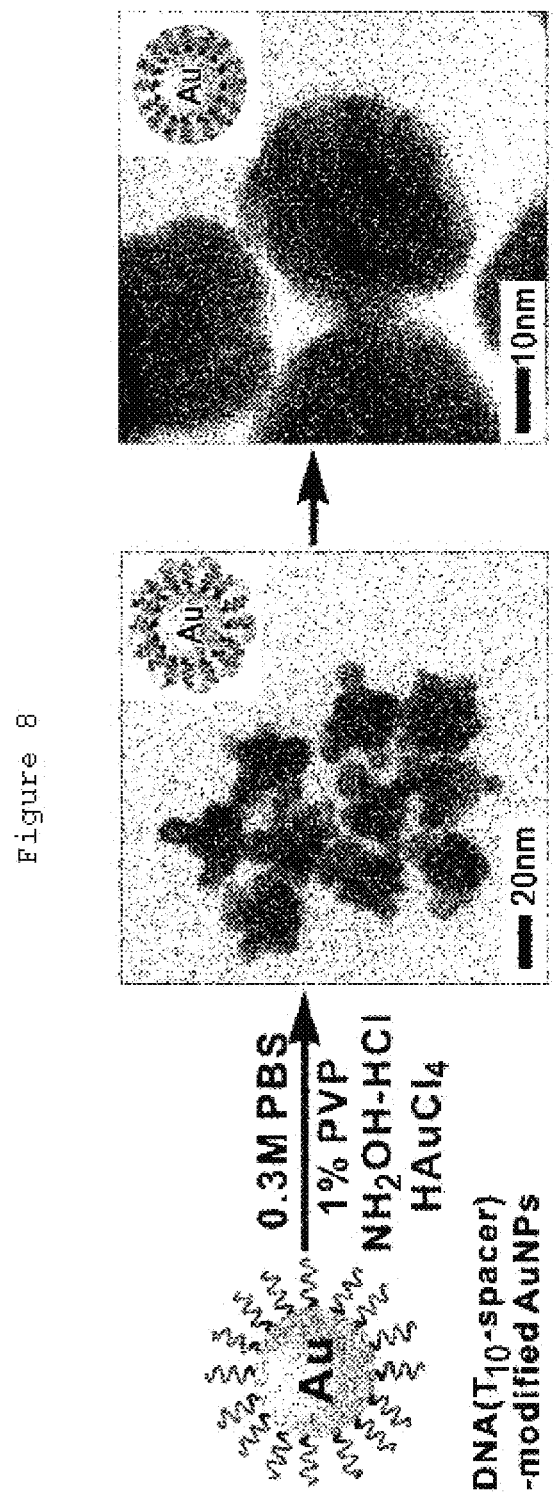
FIG. 8 represents TEM image of nanoparticle prepared using T10-oligonucleotide modified gold nanoparticle as seed.

Nanoparticle was prepared by the same method as in Example 1, except using $T_{10}$ spacer instead of $A_{10}$ spacer. In this case, single-nucleated nanostructure (Intermediate 1) was not observed in the presence of a small amount of precursor (FIG. 8). If larger amounts of precursor were used, multiple nucleation sites were formed on the surface of gold core and intra-nanogap was not formed in the final nanostructure.

Based on higher affinity to the gold surface of adenine than thymine, thymine, when used as a spacer, is expected to have approximately 40% higher DNA loading ability than when adenine is used as a spacer ((1) SJ Hurst, A K R Lytton-Jean, C A Mirkin, Anal. Chem. 78, 8313 (2006); (2) Z. Wang, J. Zhang, J M Ekman, P J A Kenis, Y. Lu, Nano Lett. DOI: 10.1021/nl100675p (2010)). The above results represent the importance of proper DNA sequence in preparing NNP nanostructure, and the formation of intra-nanobridge and nanogap is considered due to the surface of thiolated DNA-modified gold core, $AuCl_4$-ion capture effect of the nucleotide base (amine-base of guanine) ((1) A. Schimanski, E. Freisinger, A. Erxleben, B. Lippert, Inorganica Chimica Acta 283, 223 (1998) (2) K R Brown, M J Natan, Langmuir 14, 726 (1998) (3) Z. Ma, S. Sui, Angew Chem. Int Ed 41, 2176 (2002)), PVP.

Example 2

Figure 9:
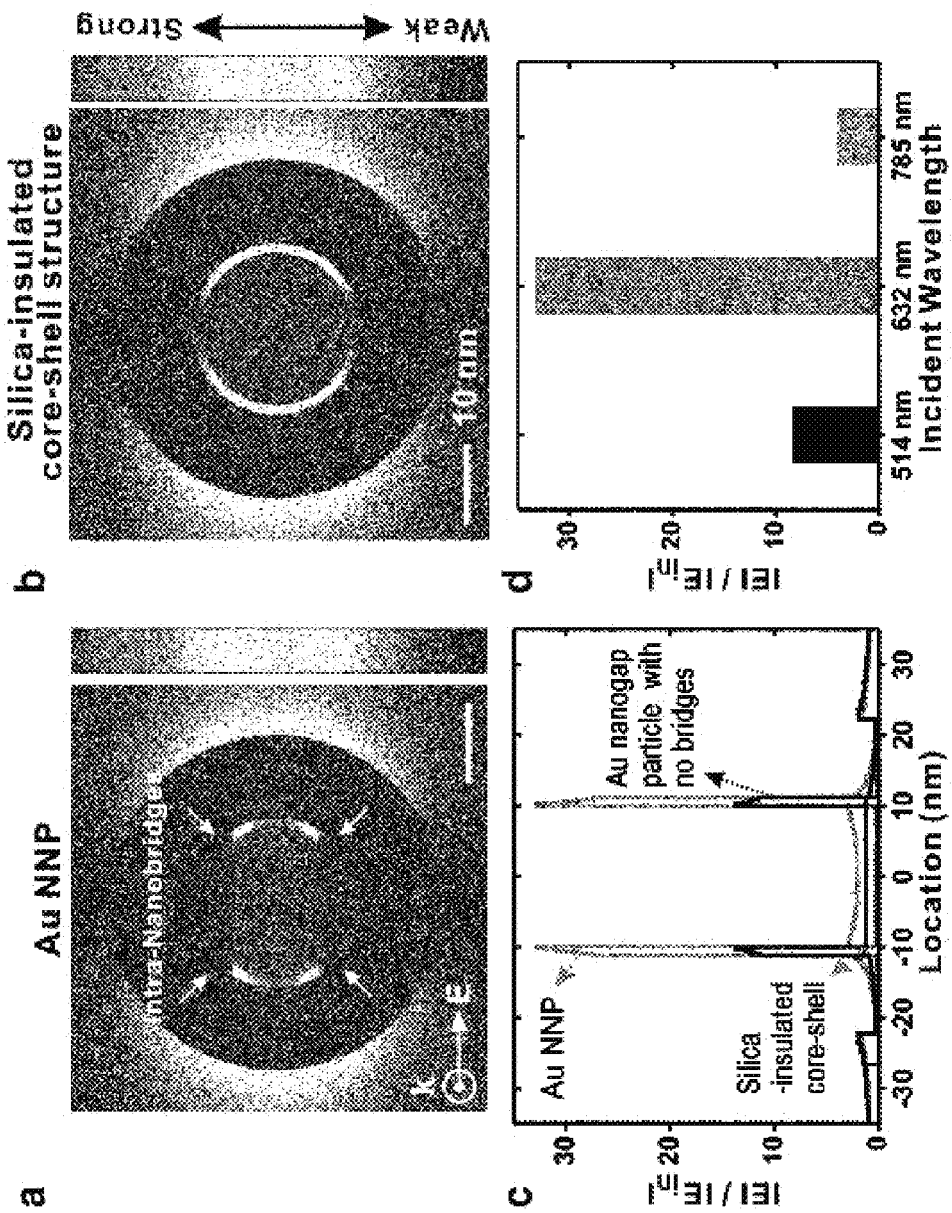
FIGS. 9a, 9b, 9c, and 9d represent calculation results of nanoparticle surrounded by NNP and silica based on 3D-FEM.
Figure 10A:
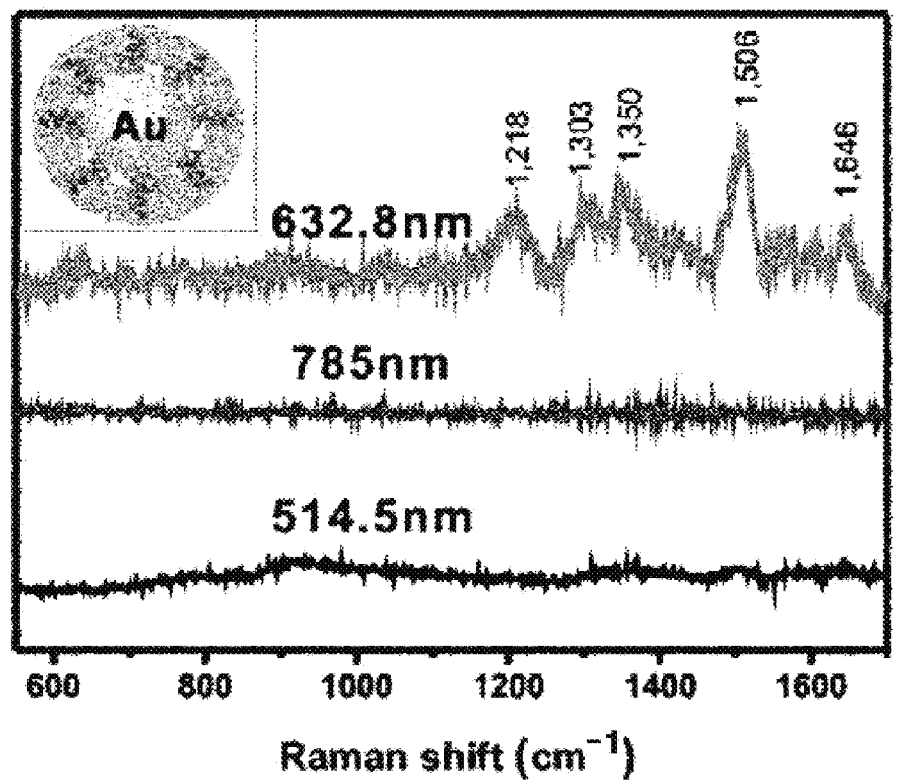
FIGS. 10a, 10b, 10c, and 10d represent a time-dependent Raman result of nanoparticle which is modified to three different kindG positions of dyes in the NNP.

Fem Calculation of Gold Nanoparticle and Core-Shell Particle Surrounded by Nanogap without Bridge and Silica In order to understand relation between Au—NNP and electromagnetic wave, FEM (3D finite-element-method was applied to the calculation (Wustholz, K. L. et al. Structure-activity relationships in gold nanoparticle dimers and trimers for surface-enhanced Raman spectroscopy. J. Am. Chem. Soc. 132, 10903-10910 (2010)), and the results were compared with Au—Au core-shell nanoparticle surrounded by silica (FIG. 9). In every calculation, four intra-nanobridges were assumed to be formed between Au core and Au shell. Radius of core is 20 nm, nanobridge is cylindrical shape of 2.5 nm×1.2 nm, size of gap or thickness of silica is 1.2 nm, and thickness of shell is 11 nm. Linearly polarized plane wave incident along the x-axis was used for plasmon excitation. The intensity of EM enhancement is represented in FIG. 9a, which indicates that EM enhancement is located intensively on the intra-gap of NNP and enhanced by maximum of 33 times of the incident light. On the other hand, in the Au—Au core-shell structure, EM is identified to be enhanced only by 3.2 times at the same area. EF values of particle surrounded by NNP and silica are $1.2 \times 10^6$ and $1.0 \times 10^2$, respectively. The calculated EF value ($1.2 \times 10^6$) can be compared with the that of "L" type trimer nano-antenna structure composed of three 100 nm gold cores and silica coating ($1.1 \times 10^6$) (Wustholz, K. L. et al. Structure-activity relationships in gold nanoparticle dimers and trimers for surface-enhanced Raman spectroscopy. J. Am. Chem. Soc. 132, 10903-10910 (2010)). Surface roughness chemical enhancement, which was not considered for the calculation, are expected to increase total SERS enhancement. The result indicates that high EM enhancement in NNP is originated from nanogap (~1.2 nm) between core and shell. Importantly, intra-nanobridge as well affects the enhancement factors. The calculation result for Au-nanogap particle without bridge is compared with that of NNP (black line in FIG. 9c), which indicates that addition of nanobridge induces the enhancement of more than $10^2$ times. Symmetry breaking could be a possible origin of this additional field enhancement. (Sonnefraud, Y. et al. Experimental realization of subradiant, superradiant, and fano resonance in ring/disk plasmonic nanocavities. ACS Nano 4, 1664-1670 (2010)). The dependence of NNP structure on the incident wavelength is studied at the three different wavelengths (514 nm, 632 nm and 785 nm; FIG. 9d). The incident wavelength of 632 nm shows the highest signal intensity. The strong independence on the wavelength coincides with the experimental result (FIG. 10a).

Example 3

Preparation of Nanoparticle with Modified Location of Raman Dye

DNA strand was used for forming platform for Raman dye modification as well as forming intra-nanogap.

Three different kinds of reduced thiolated oligonucleotides with modified location of dye ($ROX_{gap}$ (760 µL, 4.3 µM): 3'-HS—$(CH_2)_3$-(ROX)-$A_{10}$-$PEG_{18}$-AAACTCTTT-GCGCAC-5'(i.e., 3'-HS—$(CH_2)_3$-(ROX)-SEQ ID No.1-$PEG_{18}$-SEQ ID No.2-5'), $ROX_{shell}$ (131 µL, 24.9 µM): 3'-HS—$(CH_2)_3$-$A_{10}$-$PEG_{18}$-(ROX)-AAACTCTTTGCG-CAC-5' (i.e., 3'-HS—$(CH_2)_3$-SEQ ID No.1-$PEG_{18}$-(ROX)-SEQ ID No.2-5') and $ROX_{outer}$ (456 µL, 7.1 µM), 3'-HS—$(CH_2)_3$-$A_{10}$-$PEG_{18}$-AAACTCTTTGCGCAC-(ROX)-5' (i.e., 3'-HS—$(CH_2)_3$-SEQ ID No.1-$PEG_{18}$-SEQ ID No.2-(ROX)-5')) was mixed with and reacted to citrate-gold nanoparticles (1 ml, 1.0 nM) for 20 minutes at room temperature, respectively. In order to obtain as final phosphate concentration of 10 mM (pH 7.4), the resultant solution was adjusted with 100 mM phosphate buffer (for $ROX_{gap}$, $ROX_{shell}$ and $ROX_{outer}$, 176 µL, 113 µL and 146 µL added, respectively), to a final concentration of 0.1% (wt/vol) SDS with 10% SDS solution (for $ROX_{gap}$, $ROX_{shell}$ and $ROX_{outer}$, 1.9 µL, 1.2 µL, and 1.6 µL added respectively). After additional reaction of the resultant solution in orbital shaker for 20 minutes, 2M NaCl solution (10 mM PB, 0.1% SDS) was added to the reaction mixture every 20 minutes at four times (0.05 M 2 times, 0.1 M 2 times) to be adjusted to 0.3M NaCl (for $ROX_{gap}$, 48.5 µL, 48.5 µL, 97 µL, 97 µL added each time; for $ROX_{shell}$, 31.1 µL, 31.1 µL, 62.3 µL, 62.3 µL added each time; for $ROX_{outer}$, 40 µL, 40 µL, 80 µL, 80 µL added each time). Only the solution with additional $ROX_{outer}$ sequence was heated in water bath (60° C.) for about 5 minutes to minimize a non-specific interaction between ROX (5(6)-carboxy-X-rhodamine N-succinimidyl ester) molecules and the gold surface. The resultant solution (colloidal) was vortexed at room temperature for a day.

Next, the resultant solution was centrifuged (12,000 rpm, 15 min), the supernatant was removed, and the precipitated was diffused in 10 mM PB solution (pH 7.4), which was repeated twice. Finally, a resultant solution was re-diffused in 0.3 M PBS (1 ml) and the concentration of particle was measured with ultraviolet-visible light spectrometer (Agilent 8453 spectrophotometer, USA). After quantifying the number of DNA loading using the fluorescence intensity of supernatant emitted by 0.1 DTT for a day (S J Hurst, A K R Lytton-Jean, C A Mirkin, Anal. Chem. 78, 8313 (2006)), approximately 100 DNA-modified gold nanoparticles were used in the following.

All Raman experiments were carried out with a nano-Raman spectroscope (Axiovert 200, Zeiss) equipped with an inverted optical microscope (D. K. Lim, K. S. Jeon, H. M. Kim, J. M. Nam, Y. D. Suh, Nature Mater. 9, 60 (2010)). Typically, a 50-fold objective lens (NA 0.5) and 300 µW laser power were used throughout the analysis.

Each sample solution (20 µL) was placed on the 384 well optical bottom plate (Nunc™, New York, USA). First, incident wavelength dependence was analyzed with an Au-g ($ROX_{gap}$)-AuNP probe (0.5 nM) shown in FIG. 10A. Although SERS signal was not observed at the excitation wavelengths of 514.5 and 785 nm, the strong SERS signal with Raman shift of 1504 and 1645 cm$^{-1}$ in ROX was observed, which coincides with the previously reported literature ((1) P. Zhang, Y. Guo, J. Am. Chem. Soc. 131, 3808 (2009); (2) C. L. Zavaleta, et al., Proc. Natl. Acad. Sci. USA 116, 13511 (2009); (3) K. Faulds, W. E. Smith, D. Graham, Anal. Chem. 76, 412 (2004)). In the case of ROX-modified gold nanoparticle without gold shell, SERS spectrum was not observed at the excitation wavelength of 632.8 nm.

Figure 10B:
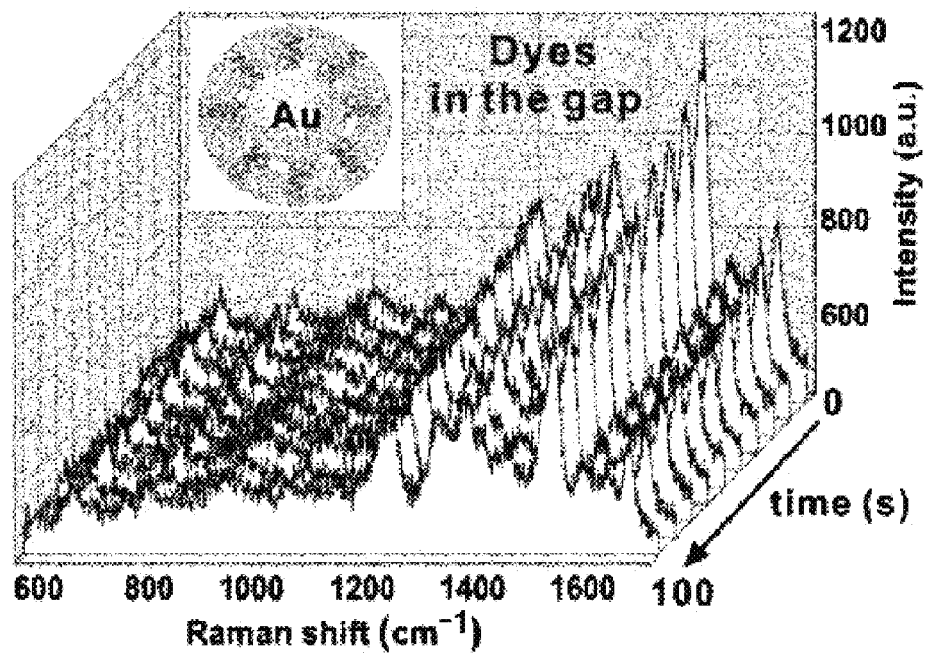
Figure 10C:
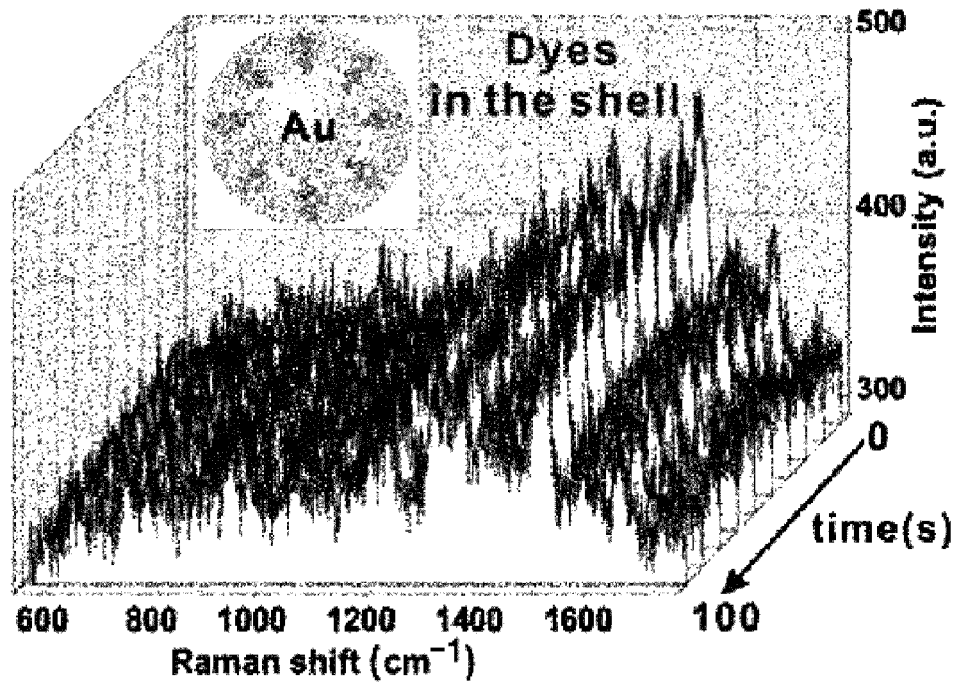
Figure 10D:
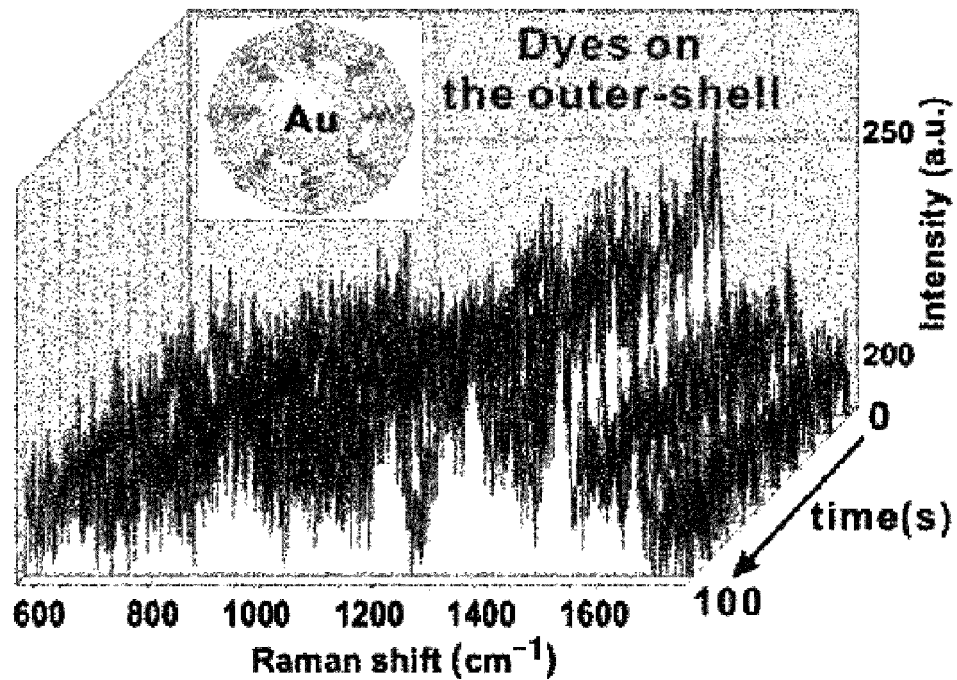

Next, the time-dependent Raman result of three different kinds of dye-modified NNP nanoparticles indicates that the signal is closely related to the location of dye in the NNP structure (FIGS. 10B, 10C and 10D). The strongest signal with excellent reproducibility was observed in the Au—NNP (ROX$_{gap}$). As the dye moves away from the intra-gap, the Raman signal weakens and reproducibility drops (Au—NNP (ROX$_{gap}$)>Au—NNP (ROX$_{shell}$)>Au—NNP (ROX$_{outer}$)).

Experimental results identified a strong SERS signal can be obtained reproducibly from Au—NNP (ROX$_{gap}$) which Raman dye is located in the intra-nanogap. In addition, signal with high uniformity and reproducibility is considered to be originated form the dye molecules which are distributed homogeneously on the surface of the core gold and quantitatively controlled. It is found that Au—S bonding between gold core and thiolated oligonucleotide and gold shell including oligonucleotide enables forming the very stable probe and confines Raman dyes uniformly to a very narrow intra-nanogap. In addition, the nanoparticles maintain the same optical characteristics at room temperature for more than 6 months.

Example 4

Preparation of Nanoparticle with Adjusted Amount of Dye

The number of Raman dyes in the intra-nanogap was adjusted as follows, characteristics were identified accordingly and the whole process was schematically shown in FIG. 11a.

It is known that if poly A spacer is used in the condition of 0.3 M PBS, the number of oligonucleotide loading on 20 nm gold nanoparticle can be approximately 100 according to the size of nanoparticle and DNA loading characteristic of DNA spacer (S. J. Hurst, A. K. R. Lytton-Jean, C. A. Mirkin, Anal. Chem. 78, 8313 (2006)). Hereupon, the mixtures of surface protecting sequence and ROX$_{gap}$-modified sequence (surface protecting sequence: 3'-HS—(CH$_2$)$_3$-A$_{10}$-PEG$_{18}$-AAACTCTTTGCGCAC-5' (i.e., 3'-HS—(CH$_2$)$_3$-SEQ ID No.1-PEG$_{18}$-SEQ ID No.2-5'), ROX$_{gap}$-modified sequence: 3'-HS—(CH$_2$)$_3$-(ROX)-A$_{10}$-PEG$_{18}$-AAACTCTTTGCG-CAC-5') (i.e., 3'-HS—(CH$_2$)$_3$-(ROX)-SEQ ID No.1-PEG$_{18}$-SEQ ID No.2-5') of four different kinds of ratio (99:1 (259 μL, 12.6 μM: 2.4 μL, 13.8 μM), 90:10 (235 μL, 12.6 μM: 24 μL, 13.8 μM), 50:50 (131 μL, 12.6 μM: 120 μL, 13.8 μM) and 0:100 (0:760 μL, 4.3 μM)) were bonded and reacted to citrate-gold nanoparticle (citrate-AuNPs; 1 ml, 1.0 nM) for 20 minutes at room temperature, respectively. In order to obtain as final phosphate concentration of 10 mM (pH 7.4), the resultant solution was adjusted with 100 mM phosphate buffer (for 99:1, 90:10, 50:50, and 0:100, 126.1 μL, 125.9 μL, 125.1 μL, and 176 μL added, respectively), to a final concentration of 0.1% (wt/vol) SDS with 10% SDS solution (for 99:1, 90:10, 50:50, and 0:100, 1.3 μL, 1.3 μL, 1.3 μL, and 1.9 μL added, respectively). After additional reaction of the resultant solution in orbital shaker for 20 minutes, 2M NaCl solution (10 mM PB, 0.1% SDS) was added to the reaction mixture every 20 minutes at four times (0.05 M twice, 0.1 M 2 times) to be adjusted to 0.3M NaCl (for 99:1, 34.7 μL, 34.7 μL, 69.4 μL, 69.4 μL added each time; for 90:10, 34.6 μL, 34.6 μL, 69.3 μL, 69.3 μL added each time; for 50:50, 34.4 μL, 34.4 μL, 68.8 μL, 68.8 μL added each time; for 0:100, 48.5 μL, 48.5 μL, 97 μL, 97 μL added each time). The resultant solution (colloidal) was vortexed at room temperature for a day.

Figure 11B:
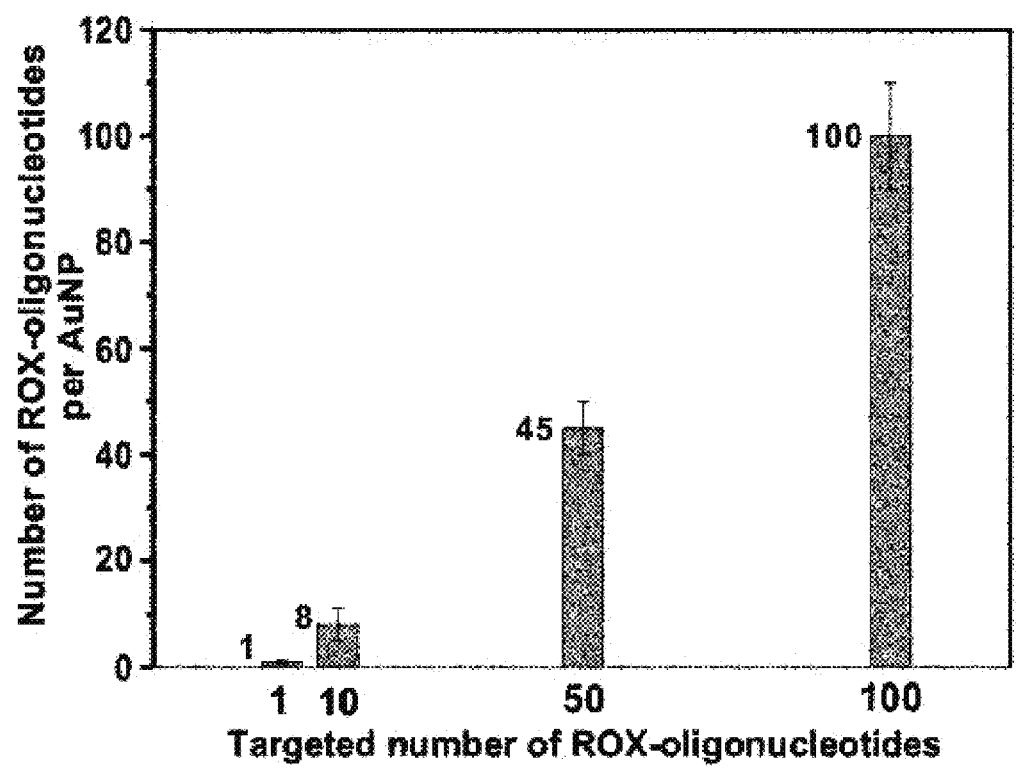
FIG. 11 represents a method for adjusting the number of Raman fluorophores.

Next, the resultant solution was centrifuged (12,000 rpm, 15 min), the supernatant was removed, and the precipitated was diffused in 10 mM PB solution (pH 7.4), which was repeated twice. Finally, a resultant solution was re-diffused in 0.3 M PBS (1 ml) and the concentration of particle was measured with ultraviolet-visible light spectrometer (Agilent 8453 spectrophotometer, USA). After quantifying the number of DNA loading using the fluorescence intensity of supernatant emitted by 0.1 DTT for a day (SJ Hurst, A K R Lytton-Jean, C A Mirkin, Anal. Chem. 78, 8313 (2006)), the result was represented in FIG. 11b. As represented in FIG. 11b, it is identified that the amount of dyes can be adjusted as intended. Prepared 100 DNA-modified gold nanoparticles were used in the following.

For all four types of concentration ratio, Au—NNP (ROX$_{gap}$) was prepared with high yield (>95%) regardless of the oligonucleotide composition, and all concentrations of NNP probes were adjusted to 0.5 nM in ultrapure water (>18MΩ).

Figure 12A:
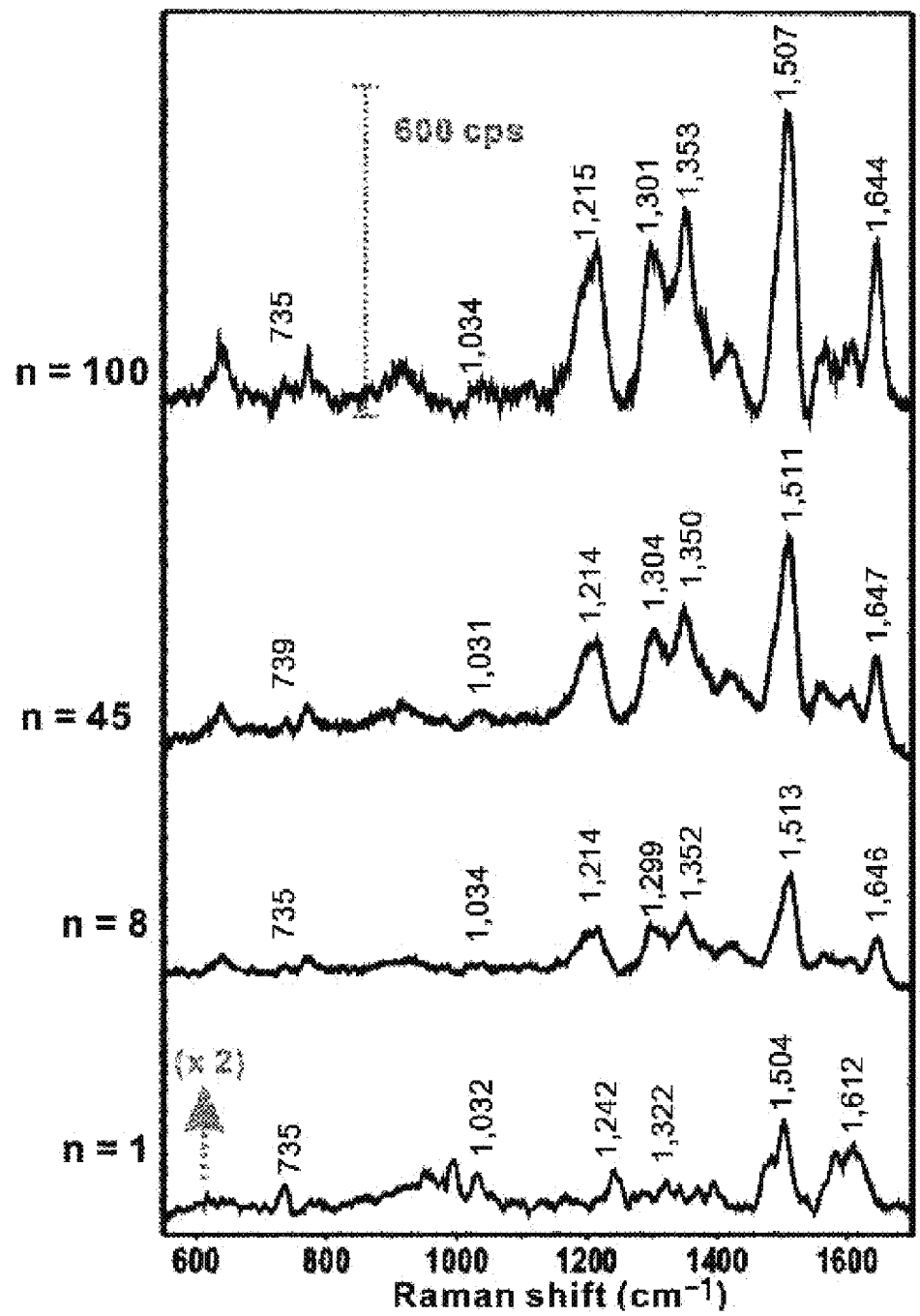
FIGS. 12a, 12b, and 12c represent the result of Raman signal of nanoparticle according the example of the present invention.
Figure 12B:
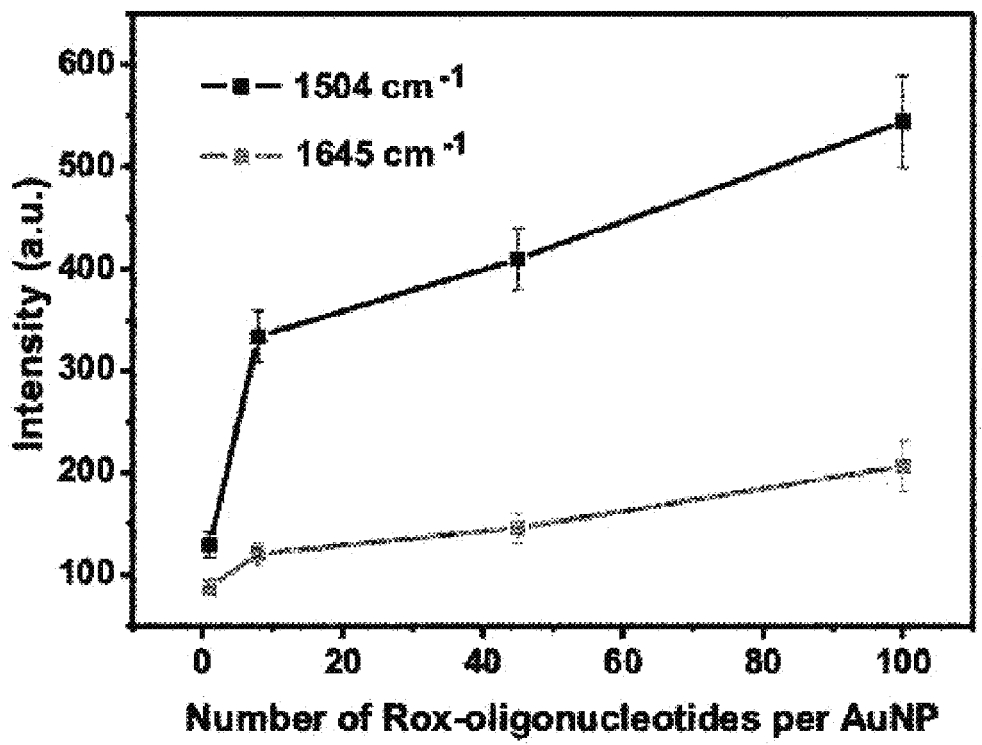

Next, Raman study based on the solution was performed for the above NNP probes (FIG. 12). When dye was not modified on the probe, the Raman signal was not detected. When only one dye was modified on the probe, small, but detectable, Raman signal was (FIG. 12a, n=1). As the number of dyes per probe increased (form n=1 to n=100), the entire spectrum intensity quantitatively increased. Characteristic spectral peak (1504 and 1645 cm$^{-1}$) was proportional to the number of ROX-modified nucleotides per probe, which indicates that the number of ROX dye per probe is proportional to the Raman signal intensity (FIG. 12b).

The above results identified that strong electromagnetic enhancement and SERS intensity by plasmon coupling between the core and the shell can be quantitatively adjusted by adjusting the number of modified dye per probe.

Example 5

Preparation of Nanoparticle with Modified Thickness of Shell

It is known that the plasmonic characteristics of metal nanoparticle can be changed by changing the structure of nanoshell. Accordingly, in order to identify the change of SERS signal depending on the thickness of shell in core-nanogap-shell structure, the particles with shell thickness of 12, 15, 20, 30, 30 and 35 nm were prepared as follows. In order to gold shell around the DNA modified gold nanoparticle core (ROX$_{gap}$-modified sequence: 3'-HS—(CH$_2$)$_3$-(ROX)-A$_{10}$-PEG$_{18}$-AAACTCTTTGCGCAC-5' (i.e., 3'-HS—(CH$_2$)$_3$-(ROX)-SEQ ID No.1-PEG$_{18}$-SEQ ID No.2-5'), number of DNA loading=100), the above DNA-modified nanoparticle (100 μL, 1 nM in 0.3M PBS) was mixed with 1% PVP solution of 50 μL. The resultant solution was mixed with hydroxylamine hydrochloride solution (10 mM) of 33.6 μL, 53 μL, 124.8 μL, 302 μL or 432 μL, and mixed with chloroauric acid solution (5 mM) of 33.6 μL, 53 μL, 124.8 μL, 302 μL or 432 μL, respectively. The reaction mixture was vortexed for 30 minutes at room temperature. After centrifugation, the concentration was adjusted to 0.5 nM with ultrapure water (18 MΩ).

Figure 12C:
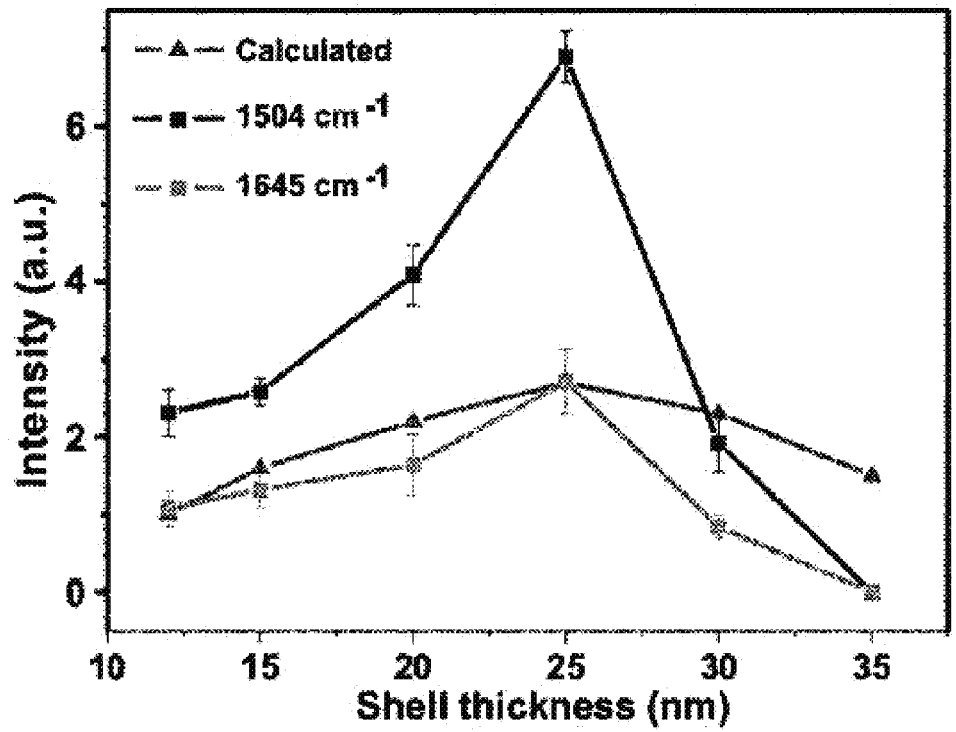

The prepared nanoparticles were analyzed at 1504 and 1645 cm$^{-1}$, respectively. As shell thickness increased from 25 nm to 12 nm, the SERS signal intensity was found to rapidly increase. However, in the case of shell thickness of >25 nm, the SERS signal began to decrease rapidly and in the case of shell thickness of 35 nm, SERS signal decrease close to almost 0 (FIG. 12c).

The above results indicated larger nanoparticles represent strong electromagnetic enhancement in some degree of SERS, which is consistent with well known fact, and reduction of electromagnetic enhancement in shell thickness of >25 nm is caused by decrease of Raman emission signal of Raman dye detected on the gap, which is because these signals need to pass through metal shell to be detected. Importantly, the whole tendency of the Raman signal changes depending on the thickness of the shell (FIG. 12c black line and red line) follows tendency of calculated area enhancement results (FIG. 12c).

Example 6

Measurement of Multiplexing Capability of Nanoparticle

In order to identify the multiplexing capability of nanoparticle according to the present invention, two types of Raman dyes (R6G-green and Cy3 dyes) were used, which were modified on oligonucleotide and placed in the nanogap.

Figure 13:
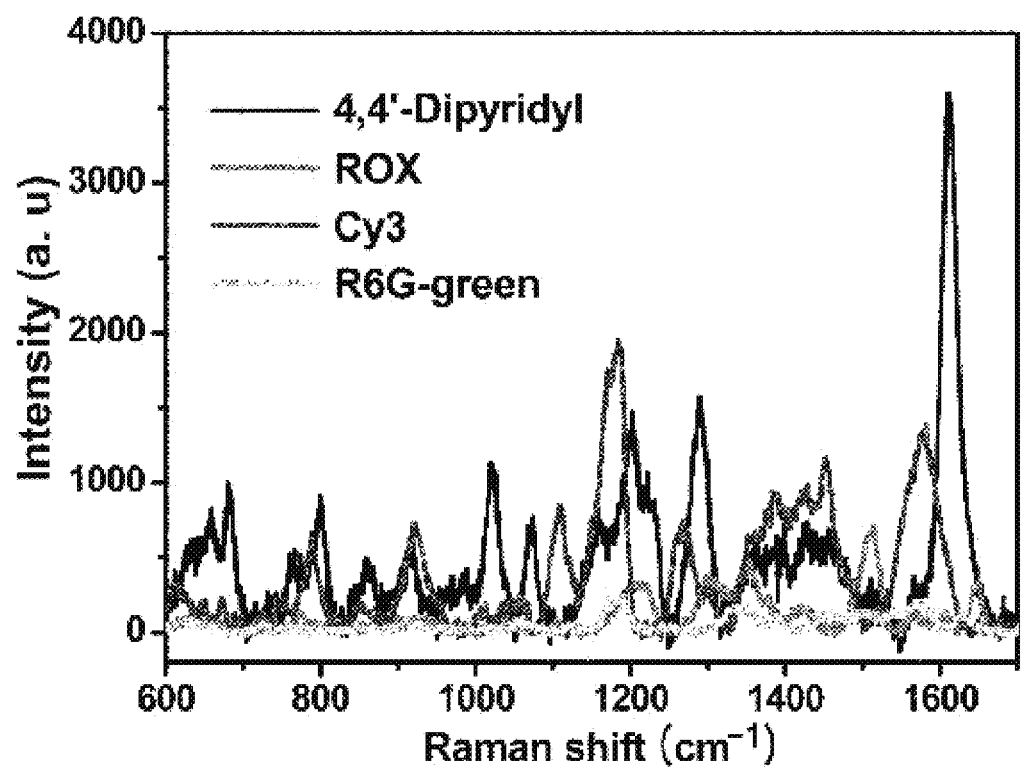
FIG. 13 represents the SERS spectrum of NNP with other fluorescent dye and non-fluorescent Raman reporter.

The same thickness of the shell (~11 nm) was used for all of the above particles, and was analyzed under the same conditions (concentration, apparatus, etc.) as for ROX dye robe. Fingerprint peaks for R6G-green and Cy3 dye probe were clearly identified; uniform time-dependent spectral pattern was confirmed for both cases. Among above three types of dyes containing ROX dye, NNP with Cy3 dye in gap (Au—NNP (Cy3) n probe (n=100)) showed the strongest SERS signal (FIG. 13).

The above results are originated from relatively large Raman cross-section of Cy3 dye in the nanogap compared with other dyes, molecular flexibility and off-resonance effect of R6G-green (Abmax=504 nm). The more dyes can be modified chemically or physically on the above gap (FIG. 14b) because large surface of intra-nanogap is available, which improves sensitivity as well as multiplexing capability.

Example 7

Figure 14A:
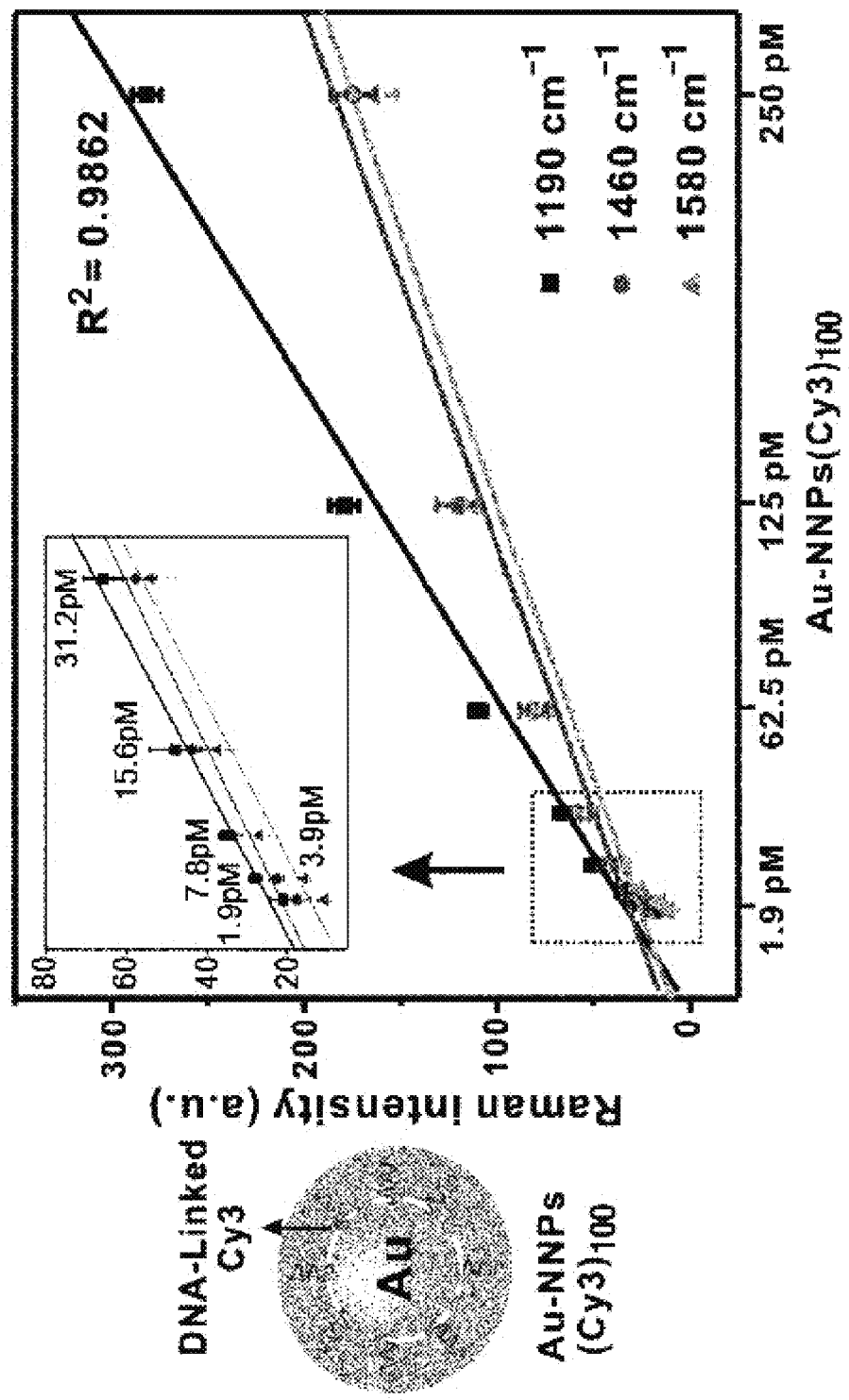
FIGS. 14a and 14b represent the intensity of Raman signal and enhancement factors according the concentration of nanoparticles according to the example of the present invention.
Figure 14B:
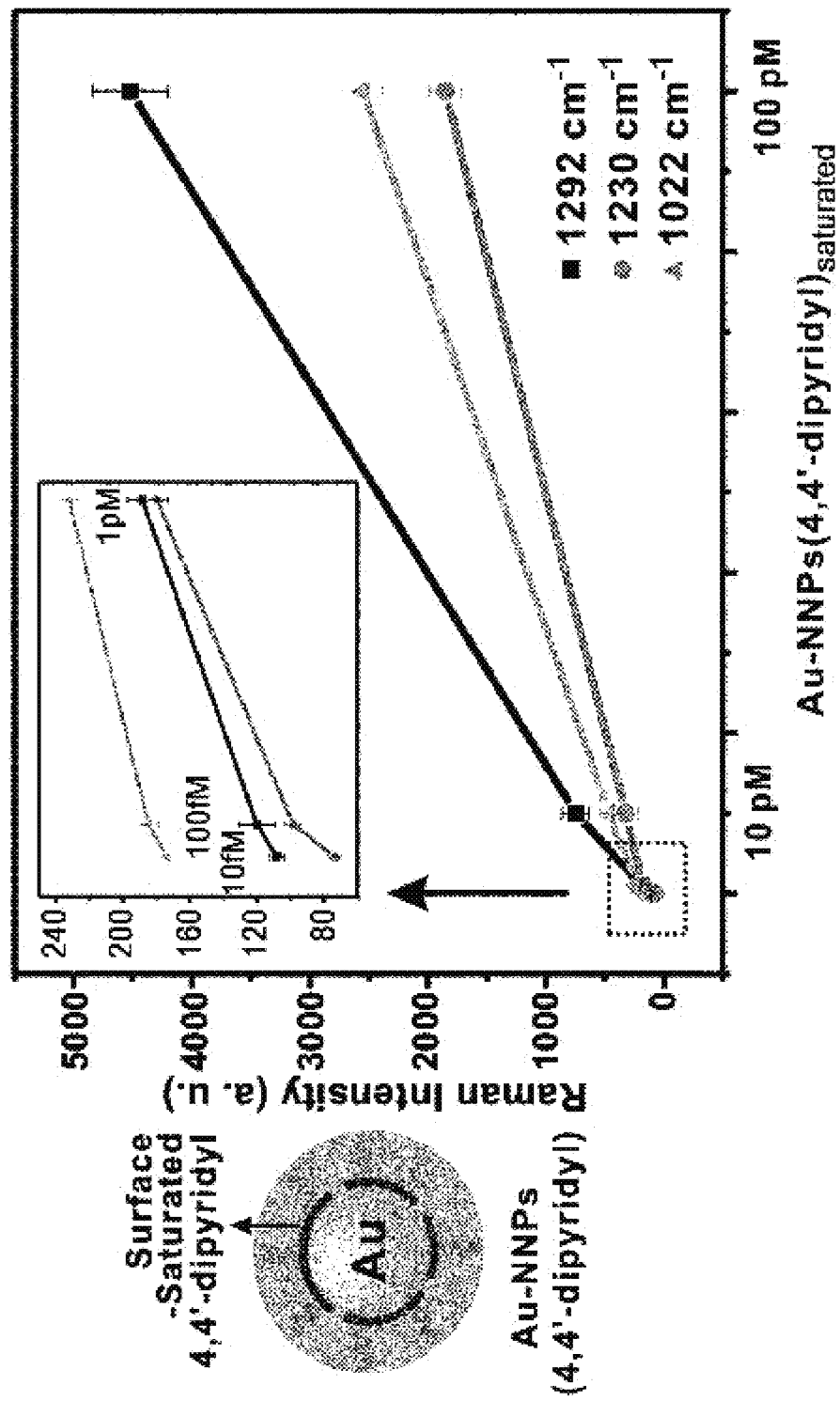
Figure 15A:
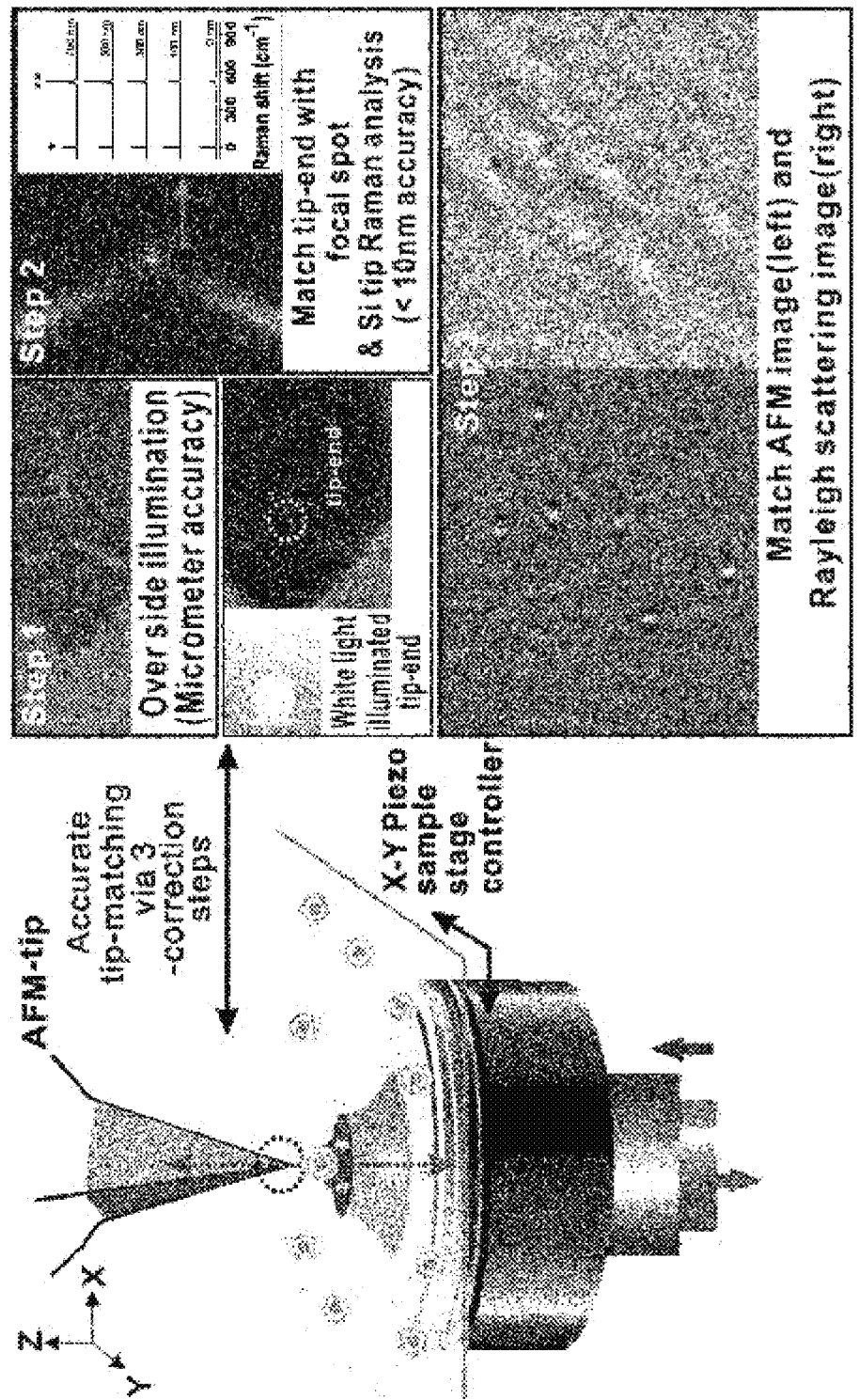
FIG. 15a represents schematically the method for AFM-correlated nano-Raman measurement.
Figure 15B:
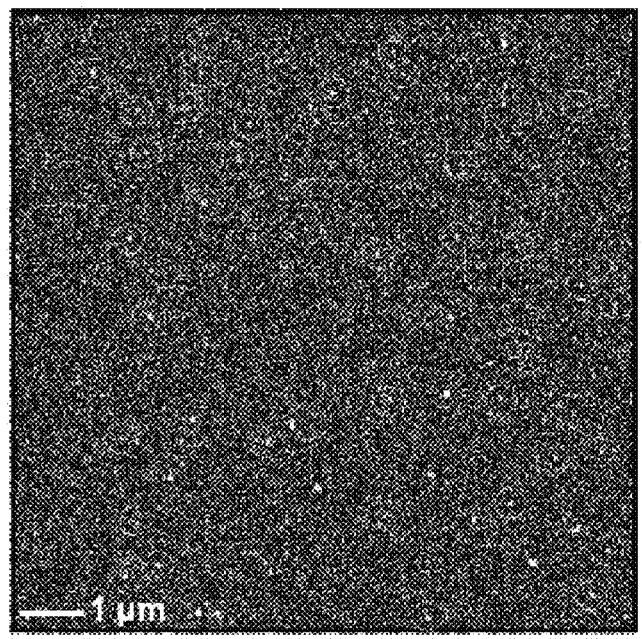
Figure 15C:
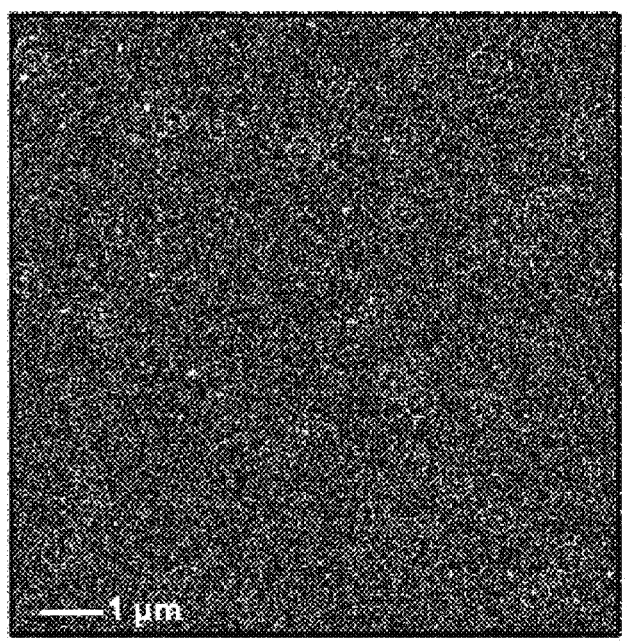
Figure 15D:
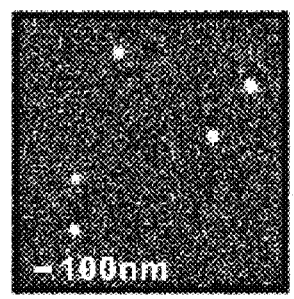
Figure 15E:
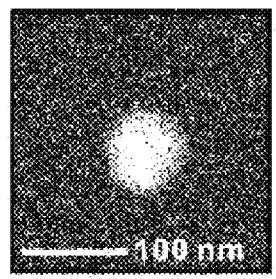
Figure 15F:
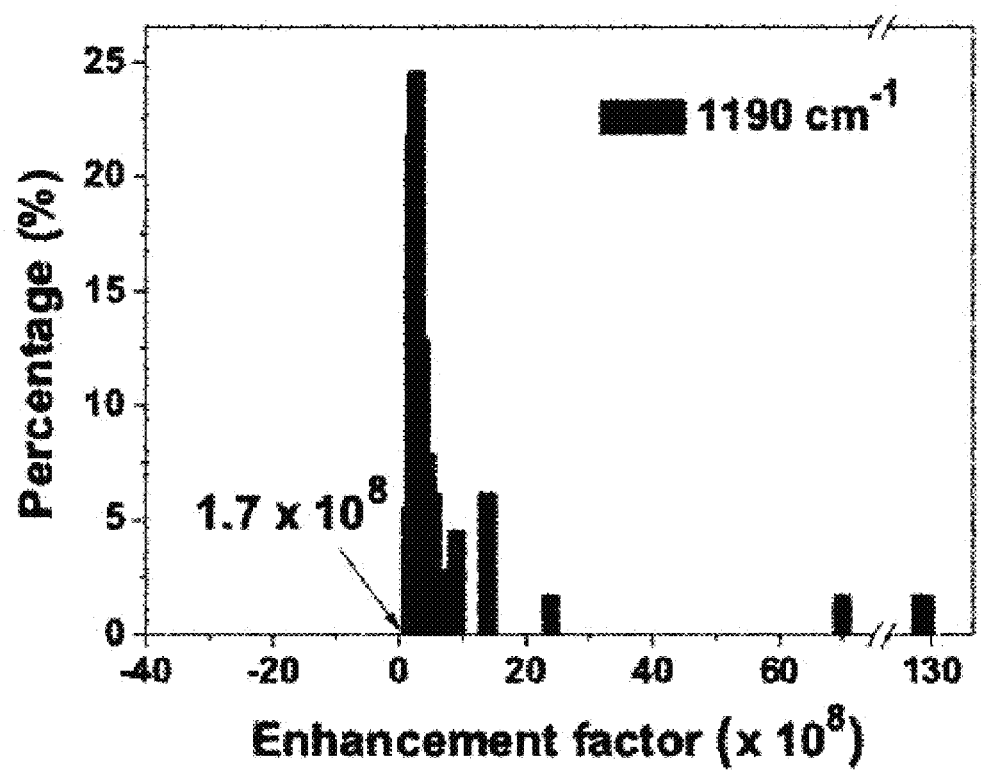
FIG. 15f to FIG. 15h represent an enhancement factor at different wavelengths in graph.
Figure 15G:
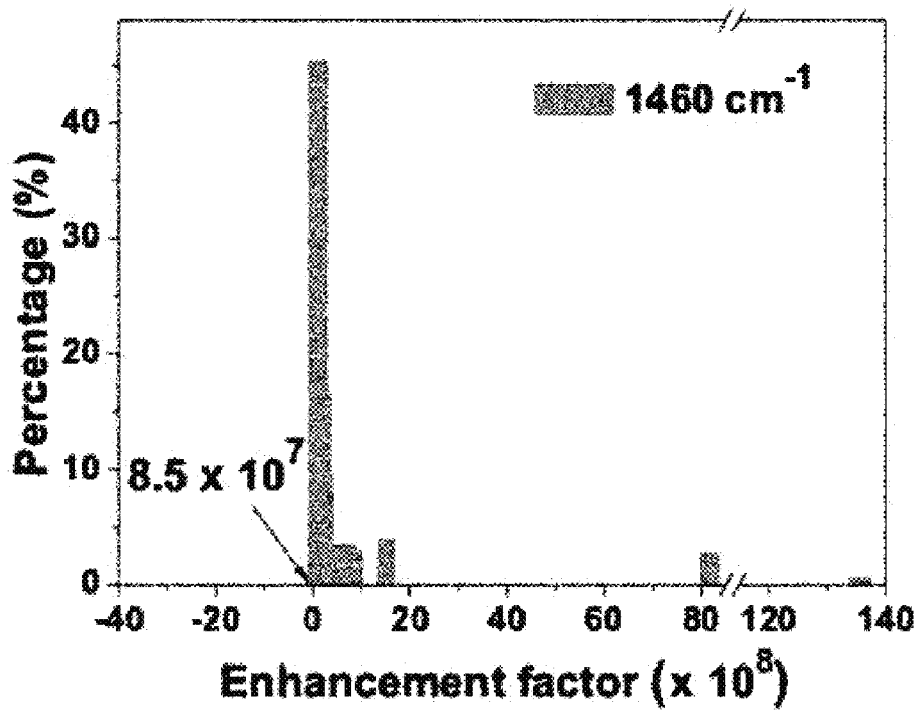
Figure 15H:
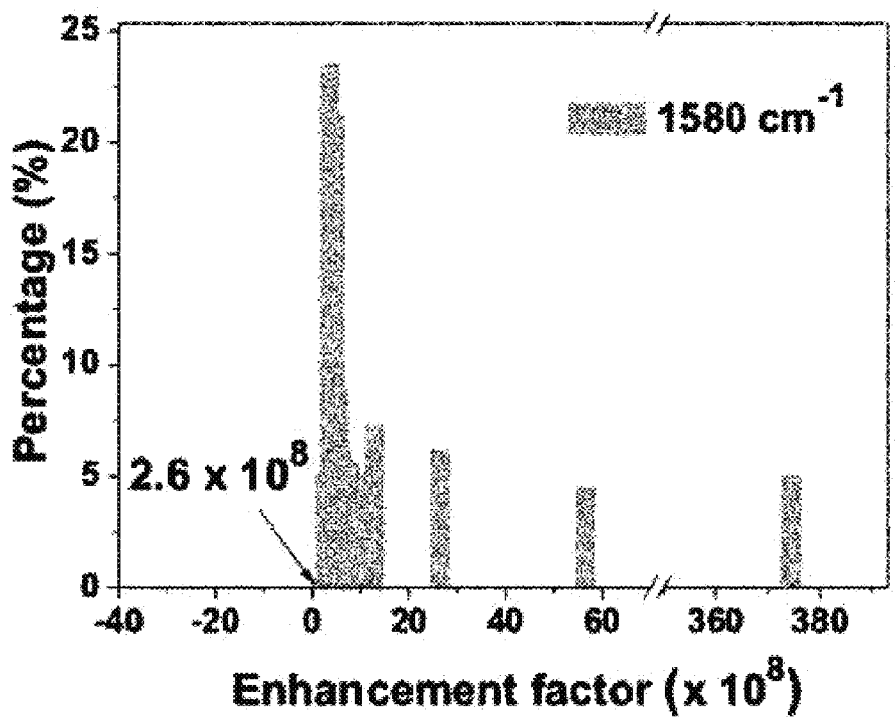

Measurement of Raman Signal According to the Concentration of the Nanoparticles and Comparison with Fluorescence-Based Detection Methods An experiment using Au—NNP(Cy3)$_{100}$ probes was carried out to identify the relation between the concentration of particles and intensity of SERS. First, the nanoparticles were washed with deionized water (18 MΩ) several times and the distribution of concentration of the particles were analyzed with 650 µW laser power and displayed in FIG. 14a. The results of Raman shift in 1190, 1460 and 1580 cm$^{-1}$ showed the outstanding relation between the concentration of particles and intensity of SERS($R^2$=0.9862) (FIG. 14a). The detection limit in the solution (1.9 pM) can be improved by using stronger laser power or increasing the number of reporter molecules in the nanogap. Unlike the conventional hot spots formed on the outer connection area between nanoparticles which limited number of Raman dyes can be located irregularly, Au—NNP according to the present invention can saturate the Raman dye molecules chemically or physically. In order to achieve higher sensitivity by using Au—NNP in solution, non-resonant Raman reporter molecule (4,4'-dipyridyl)-saturated Au—NNP was used. In order to prepare 4,4'-dipyridyl saturated Au—NNP, oligonucleotides (3'-HS—(CH$_2$)$_3$-A$_{10}$-PEG$_{18}$-AAACTCTTT-GCGCAC-5', i.e., 3'-HS—(CH$_2$)$_3$-SEQ ID No.1-PEG$_{18}$-SEQ ID No.2-5') was first modified on the surface of AuNP core. After mixing DNA-AuNPs (500 µL of 1.0 nM) with 100 µL of 4,4'-dipyridyl solution (0.1 M, ultrapure water water), the resultant solution was incubated for 3 days with gentle shaking at the room temperature. Excess of 4,4'-dipyridyl was removed by repeated centrifugal filtration (15 min, 12,000 rpm) and re-diffusion in 0.3M PBS, and Au shell was formed successfully. 4,4'-dipyridyl molecules was bonded physically on the surface of the core of AuNP and saturated before Au shell formation. Due to smaller molecular size and higher coating weight than Cy3, the higher sensitivity can be provided (FIG. 10). Linear relationship between probe concentration and Raman intensity was observed. As a very important result, the Raman signal was measured at 10 fM solution as well (4,4'-dipyridyl fingerprint peak was clearly identified at 1292 cm$^{-1}$, 1230 cm$^{-1}$, and 1022 cm$^{-1}$. The results identified that the particles represent stable SERS signal and a very highly sensitive and quantitative SERS spectrum.

The invention claimed is:

1. A nanoparticle comprising
   a core,
   a shell surrounding the core,
   a linear polymer connected to the core, wherein the polymer comprises:
      an alkyl thiol end segment attached to the core in which a thiol group of the alkyl thiol end segment is attached to the linear polymer;
      a Raman active fluorescent dye covalently attached to an alkyl group of the alkyl thiol end segment; and
      a spacer oligonucleotide segment covalently attached to the Raman active fluorescent dye;
   nanobridges connecting between the core and the shell, each nanobridge being composed of the same metal as the shell,
   a nanogap formed between the core and shell in which the Raman active fluorescent dye is positioned within the nanogap,
   wherein the core and shell are independently composed of the metal showing surface plasmon reasonance.

2. The nanoparticle according to claim 1, wherein the diameter of the core is 1 nm to 900 nm.

3. The nanoparticle according to claim 1, wherein the thickness of the shell is 1 nm to 900 nm.

4. The nanoparticle according to claim 1, wherein the spacer oligonucleotide segment comprises SEQ ID No. 1.

5. The nanoparticle according to claim 4, wherein the linear polymer further comprises a polyethylene glycol segment covalently attached to the spacer oligonucleotide segment.

6. The nanoparticle according to claim 5, wherein the linear polymer further comprises a 5' oligonucleotide end segment attached to the polyethylene glycol segment.

7. The nanoparticle according to claim 6, wherein the 5' oligonucleotide end segment comprises SEQ ID No 2.

8. The nanoparticle according to claim 1, further comprising a non-fluorescent Raman reporter positioned within the nanogap.

9. The nanoparticle according to claim 8, wherein the non-fluorescent Raman reporter comprises 4,4'-Diphyridyl.

10. The nanoparticle according to claim 1, wherein the diameter of the nanoparticle is 1 nm to 990 nm.

11. The nanoparticle according to claim 1, further comprising one selected from the group consisting of a CT contrast agent, an MRI contrast agent, an optical contrast agent and an ultrasonic contrast agents inside or outside of the nanoparticle.

12. The nanoparticle according to claim 1, further comprising one selected from the group comprising genes, antibodies, and drugs.

13. The nanoparticle according to claim 1, wherein the Raman active fluorescent dye is selected from the group consisting of FAM, Dabcyl, TRITC (tetramethyl rhodamine-5-isothiocyanate), MGITC (malachite green isothiocyanate), XRITC (X-rhodamine-5-isothiocyanate), DTDC (3,3-diethylthiadicarbocyanine iodide), TRIT (tetramethyl rhodamine isothiol), NBD (7-nitrobenz-2-1,3-diazol), phthalic acid, terephthalic acid, isophthalic acid, para-aminobenzoic acid, erythrocin, biotin, digoxigenin, 5-carboxy-4',5'-dichloro-2',7'-dimethoxy, fluorescein, 5-carboxy-2',4',5',7'-tetrachlorofluorescein, 5-carboxyfluorescein, 5-carboxyrhodamine, 6-carboxyrhodamine, 6-carboxytetramethyl amino phthalocyanine, azomethine, cyanine (Cy3, Cy3.5, Cy5), xanthine, succinylfluorescein, and aminoacridine.

14. The nanoparticle according to claim 1, wherein the Raman active fluorescent dye is selected from the group consisting of ROX, Cy3, Cy3.5, Cy5 and R6G-green.

15. A nanoparticle comprising
    a core;
    a shell surrounding the core;
    a linear polymer connected to the core, wherein the linear polymer comprises:
       an alkyl thiol end segment attached to the core in which a thiol group of the alkyl thiol end segment is covalently attached to the core;
       a Raman active fluorescent dye covalently attached to an alkyl group of the alkyl thiol end segment;
       a spacer oligonucleotide segment covalently attached to the Raman active fluorescent dye;
       a polyethylene glycol segment covalently attached to the spacer oligonucleotide segment; and
       a 5' oligonucleotide end segment covalently attached to the polyethylene glycol segment;
    nanobridges connecting between the core and the shell, each nanobridge being composed of the same metal as the shell, and
    a nanogap formed between the core and shell in which the Raman active fluorescent dye is positioned within the nanogap.

16. The nanoparticle according to claim 15, wherein the Raman active fluorescent dye is selected from the group consisting of ROX, Cy3, Cy3.5, Cy5 and R6G-green.

17. The nanoparticle according to claim 15, further comprising a non-fluorescent Raman reporter positioned in the nanogap, wherein the non-fluorescent Raman reporter comprises 4,4'-Diphyridyl.

18. The nanoparticle according to claim 15, wherein the Raman active fluorescent dye is selected from the group consisting of FAM, Dabcyl, TRITC (tetramethyl rhodamine-5-isothiocyanate), MGITC (malachite green isothiocyanate), XRITC (X-rhodamine-5-isothiocyanate), DTDC (3,3-diethylthiadicarbocyanine iodide), TRIT (tetramethyl rhodamine isothiol), NBD (7-nitrobenz-2-1,3-diazol), phthalic acid, terephthalic acid, isophthalic acid, para-aminobenzoic acid, erythrocin, biotin, digoxigenin, 5-carboxy-4',5'-dichloro-2',7'-dimethoxy, fluorescein, 5-carboxy-2',4',5',7'-tetrachlorofluorescein, 5-carboxyfluorescein, 5-carboxyrhodamine, 6-carboxyrhodamine, 6-carboxytetramethyl amino phthalocyanine, azomethine, cyanine (Cy3, Cy3.5, Cy5), xanthine, succinylfluorescein, and aminoacridine.

19. The nanoparticle according to claim 15, wherein
the alkyl thiol end segment comprises —S—$(CH_2)_3$—;
the spacer oligonucleotide segment comprises SEQ ID No 1;
the polyethyelene glycol segment comprises ($PEG_{18}$); and
the 5' oligonucleotide end segment comprises SEQ ID No 2.

20. A nanoparticle comprising
a core;
a shell surrounding the core;
a linear polymer connected to the core, wherein the linear polymer comprises:
   an alkyl thiol end segment attached to the core in which a thiol group of the alkyl thiol end segment is covalently attached to the core, wherein the alkyl thiol end segment comprises —S—$(CH_2)_3$—;
   a Raman active fluorescent dye covalently attached to an alkyl group of the alkyl thiol end segment; and
   a spacer oligonucleotide segment covalently attached to the Raman active fluorescent dye wherein the spacer oligonucleotide segment comprises SEQ ID No 1;
   a polyethylene glycol segment covalently attached to the spacer oligonucleotide segment wherein the polyethyelene glycol segment comprises ($PEG_{18}$); and
   a 5' oligonucleotide end segment covalently attached to the polyethylene glycol segment wherein the 5' oligonucleotide end segment comprises SEQ ID No 2;
nanobridges connecting between the core and the shell, each nanobridge being composed of the same metal as the shell, and
a nanogap formed between the core and shell in which the Raman active fluorescent dye is positioned within the nanogap.

* * * * *

SEQUENCE LISTING

<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Spacer oligonucleotides

<400> SEQUENCE: 1
aaaaaaaaaa                                                          10

<210> SEQ ID NO 2
<211> LENGTH: 15

```
<212> TYPE: DNA
<213> ORGANISM: Artificial Sequence
<220> FEATURE:
<223> OTHER INFORMATION: 5' oligonucleotide end segment

<400> SEQUENCE: 2
aaactctttg cgcac                                                        15
```